(12) United States Patent
Hitschmann

(10) Patent No.: US 11,278,453 B2
(45) Date of Patent: Mar. 22, 2022

(54) COMPRESSION DEVICE

(71) Applicant: 3M INNOVATIVE PROPERTIES COMPANY, Saint Paul, MN (US)

(72) Inventor: Guido Hitschmann, Neuss (DE)

(73) Assignee: 3M INNOVATIVE PROPERTIES COMPANY, Saint Paul, MN (US)

(*) Notice: Subject to any disclaimer, the term of this patent is extended or adjusted under 35 U.S.C. 154(b) by 1211 days.

(21) Appl. No.: 15/512,133

(22) PCT Filed: Sep. 18, 2015

(86) PCT No.: PCT/US2015/050945
§ 371 (c)(1),
(2) Date: Mar. 17, 2017

(87) PCT Pub. No.: WO2016/048827
PCT Pub. Date: Mar. 31, 2016

(65) Prior Publication Data
US 2017/0273830 A1    Sep. 28, 2017

(30) Foreign Application Priority Data
Sep. 23, 2014 (GB) ..................................... 1416782

(51) Int. Cl.
*A61F 13/00* (2006.01)
*A61F 5/01* (2006.01)
*A61F 13/08* (2006.01)
*A61F 13/06* (2006.01)
(Continued)

(52) U.S. Cl.
CPC ...... *A61F 13/00038* (2013.01); *A61F 5/0109* (2013.01); *A61F 13/062* (2013.01);
(Continued)

(58) Field of Classification Search
CPC . A61H 9/005; A61F 5/0109; A61F 13/00038; A61F 13/08; A61F 13/085;
(Continued)

(56) References Cited

U.S. PATENT DOCUMENTS 3,538,914 A    11/1970   Myers
3,845,769 A    11/1974   Shaw
(Continued)

FOREIGN PATENT DOCUMENTS

CN    103648568    3/2014
EP    1974704      10/2008
(Continued)

OTHER PUBLICATIONS

Partsch et al: "Classification of Compression Bandages: Practical Aspects"; Dermatologic Surgery—Jun. 2008; pp. 600-609 (Year: 2008).*

(Continued)

*Primary Examiner* — Caitlin A Carreiro
(74) *Attorney, Agent, or Firm* — 3M Innovative Properties Company; Trisha D. Adamson

(57) ABSTRACT

A compression system for applying compression to a body part of a user. The compression system has a sleeve for substantially covering a portion of the body part of a user. The sleeve has two lateral side edges. In the transverse direction from the first lateral side edge to the second lateral side edge the sleeve has a first lateral side region, a central region and a second lateral side region. At least the central region of the sleeve has a material with elasticity in the transverse direction and longitudinal direction of the sleeve. The compression system has a releasable closure system. Upon closure of the closure system the sleeve is restrained and tightened about the body part of the user.

15 Claims, 10 Drawing Sheets

(51) Int. Cl.
*A61F 13/10* (2006.01)
*A61F 13/15* (2006.01)
(52) U.S. Cl.
CPC .......... *A61F 13/085* (2013.01); *A61F 13/108* (2013.01); *A61F 2013/15284* (2013.01); *A61F 2013/15292* (2013.01); *A61F 2013/15357* (2013.01)
(58) Field of Classification Search
CPC ...... A61F 13/06; A61F 13/061; A61F 13/062; A61F 13/00004; A61F 13/00034; A61F 13/108; A61F 13/00; A61F 13/00008; A61F 13/00021; A61F 13/107; A61F 13/101; A61F 13/102; A61F 13/066; A61F 5/01; A61F 5/0102; A61F 5/0104; A61F 5/0106; A61F 5/0118; A61F 5/013; A61F 5/05866; A61F 5/0585; A61F 5/0123; A61F 5/0111; A61F 5/0127; A61F 2013/15284; A61F 2013/15292; A61F 2013/15357; A61F 2013/15203; A61F 2013/15325; A61F 2013/00119; A61F 2013/00238; B32B 5/04; B32B 2307/51; B32B 2307/50; B32B 2307/54; D02G 3/32; D02G 3/326; D03D 15/56; D03D 15/573; D03D 2700/0103; D03D 7/00; D03D 17/00; D10B 2401/061; D04B 1/00; D04B 1/265; D04B 21/00; D04B 1/24; D04B 1/18; D04B 21/18; A41D 13/00; A41D 13/08; A41D 27/10
USPC ..... 602/53, 75, 5, 21, 25–27, 41, 60–65, 76; 442/182, 184, 304, 306, 328–329; 2/69, 2/16, 22, 311, 59, 125; 600/20; 66/170, 66/171, 172 E, 178 A; 428/34.1, 36.1, 428/36.9
See application file for complete search history.

(56) References Cited

U.S. PATENT DOCUMENTS

| 5,254,122 | A | 10/1993 | Shaw |
| 5,267,943 | A | 12/1993 | Dancyger |
| 6,152,893 | A | 11/2000 | Pigg |
| 2005/0192524 | A1 | 9/2005 | Lipshaw |
| 2005/0209545 | A1 | 9/2005 | Farrow |
| 2007/0179421 | A1 | 8/2007 | Farrow |
| 2010/0143652 | A1* | 6/2010 | Stockton ............... A61K 8/8111 428/141 |
| 2010/0312160 | A1* | 12/2010 | Creighton ............... A61L 15/42 602/62 |
| 2013/0066286 | A1* | 3/2013 | Croizat ............... A61M 1/0088 604/319 |
| 2013/0218060 | A1* | 8/2013 | Bushby ................. A61F 5/0118 602/21 |
| 2013/0319128 | A1 | 12/2013 | Richardson |

FOREIGN PATENT DOCUMENTS

| EP | 2275062 A2 * | 1/2011 | ............ A61F 13/08 |
| GB | 2473321 | 3/2011 | |
| JP | H06-319791 | 11/1994 | |
| JP | 2010-229584 | 10/2010 | |
| JP | 2013-144860 | 7/2013 | |
| JP | 2013-252199 | 12/2013 | |
| WO | WO 1997-46181 | 12/1997 | |
| WO | WO 2001-72250 | 10/2001 | |
| WO | WO-0172250 A1 * | 10/2001 | ........... A61F 13/085 |
| WO | WO 2006-110527 | 10/2006 | |
| WO | WO 2007-065435 | 6/2007 | |
| WO | WO 2009/094037 | 7/2009 | |
| WO | WO 2010-117723 | 10/2010 | |
| WO | WO 2011-066237 | 6/2011 | |
| WO | WO 2013/001506 | 1/2013 | |
| WO | WO 2014-116497 | 7/2014 | |
| WO | WO 2014-132127 | 9/2014 | |
| WO | WO-2014132127 A1 * | 9/2014 | ........... A61F 13/085 |
| WO | WO 2014-160572 | 10/2014 | |
| WO | WO 2014/202161 | 12/2014 | |
| WO | WO 2016-003790 | 1/2016 | |

OTHER PUBLICATIONS

International Search Report for PCT International Application No. PCT/US2015/050945, dated Dec. 4, 2015, 5pgs.
Search Report for CN201580051425.8 dated Aug. 31, 2018, 3 pgs.

\* cited by examiner

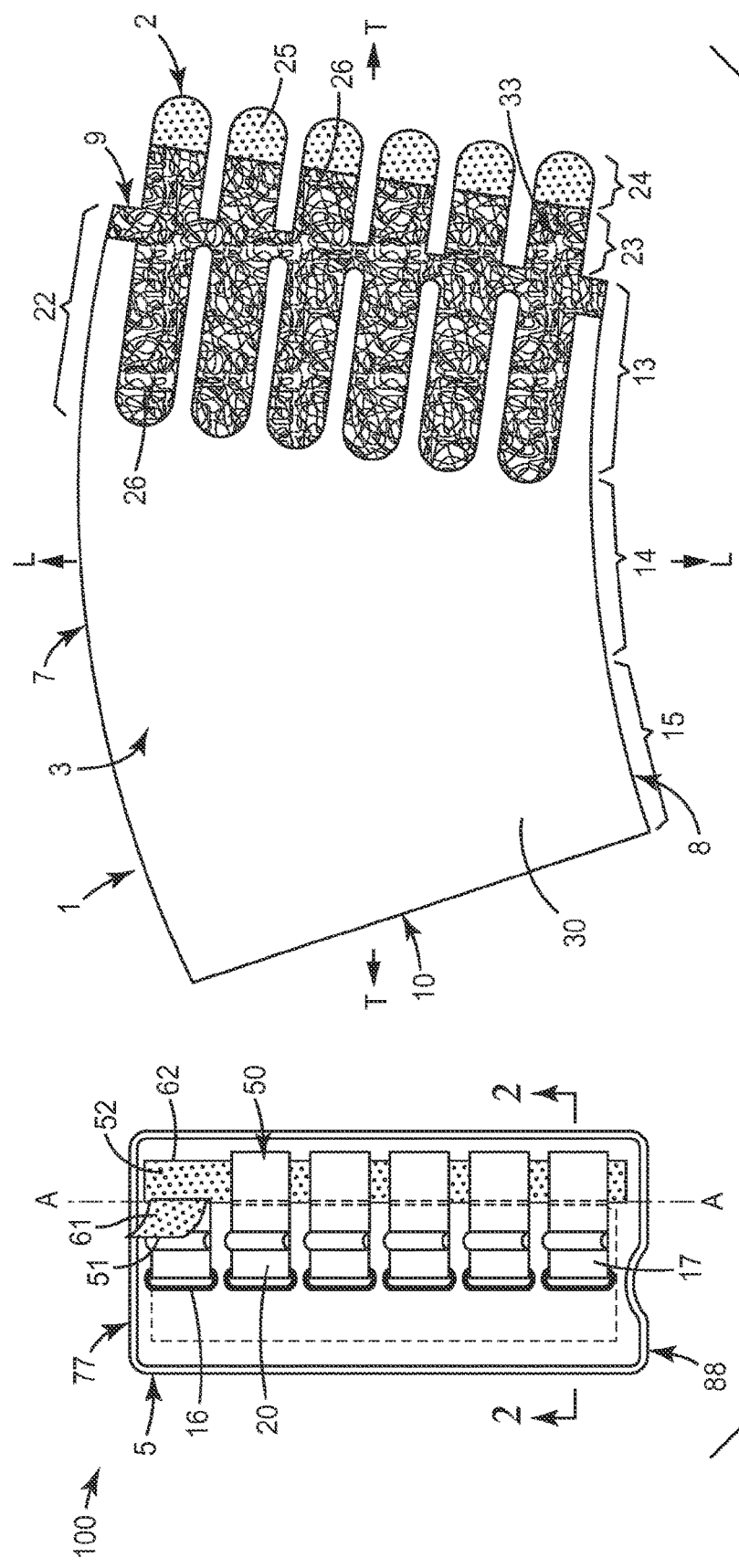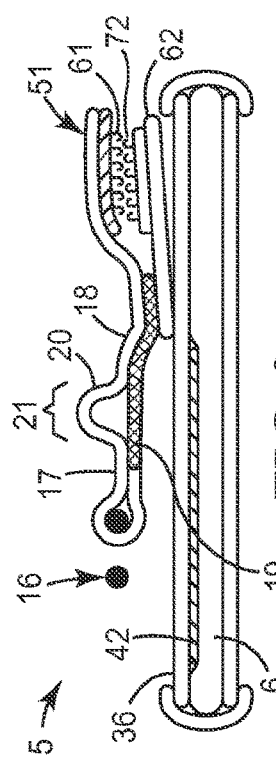

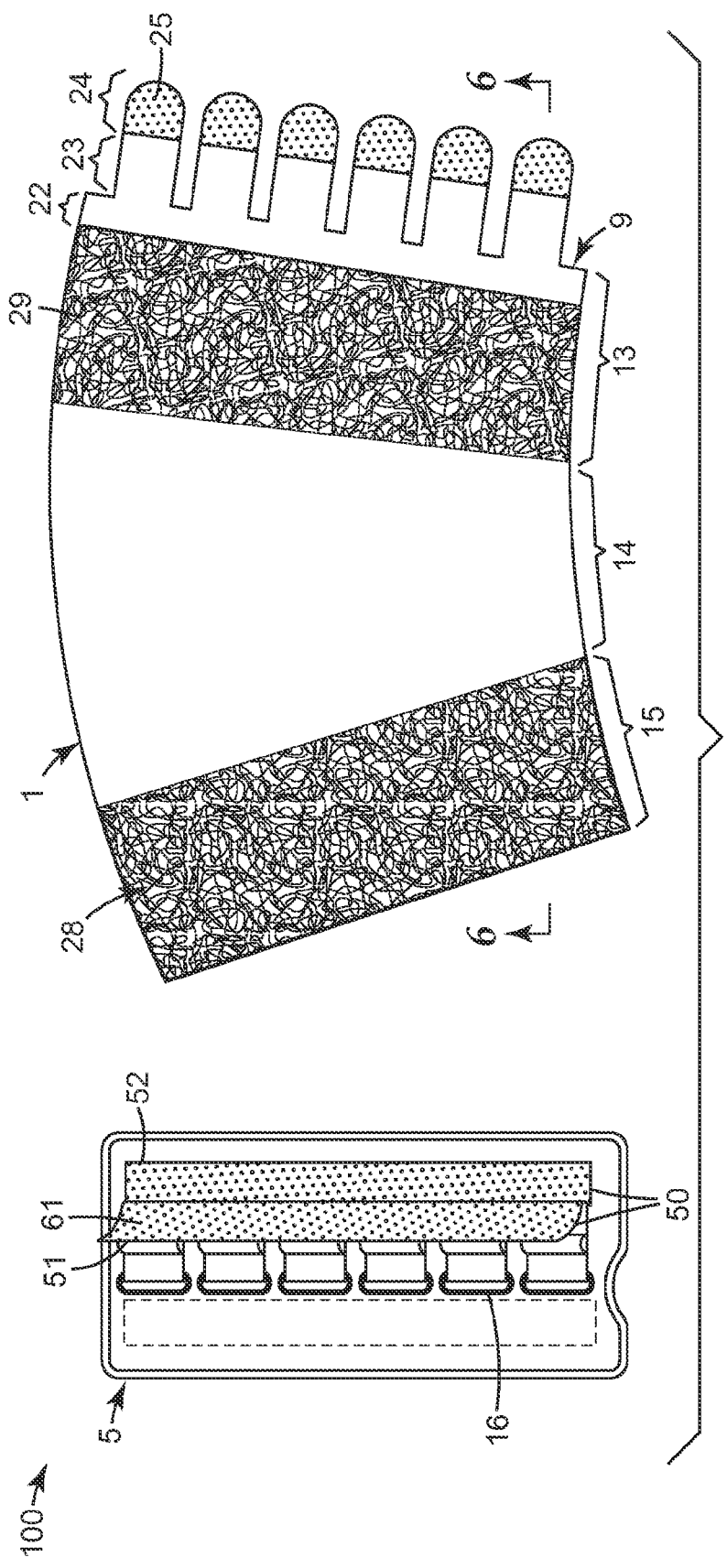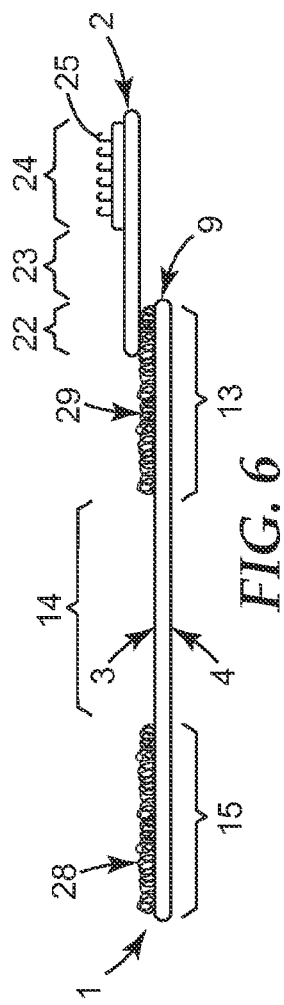
FIG. 5
FIG. 6

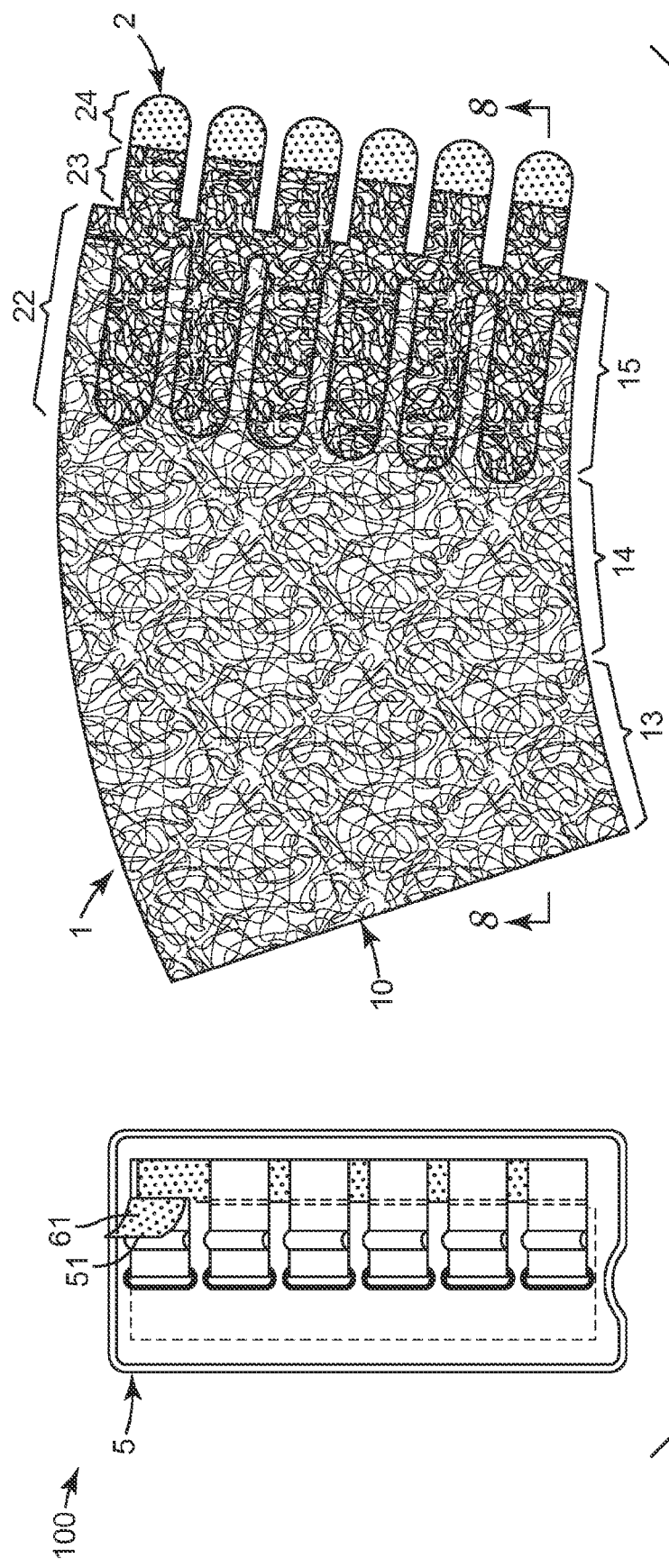
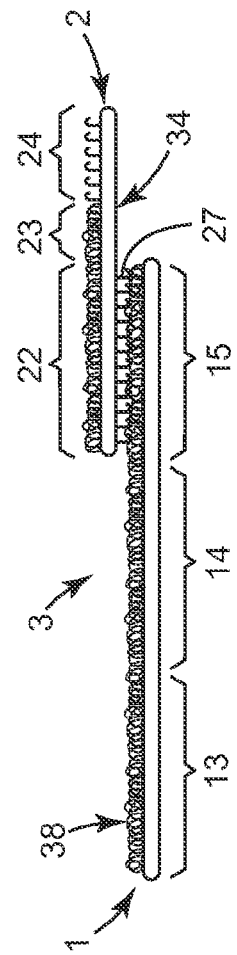
FIG. 7
FIG. 8

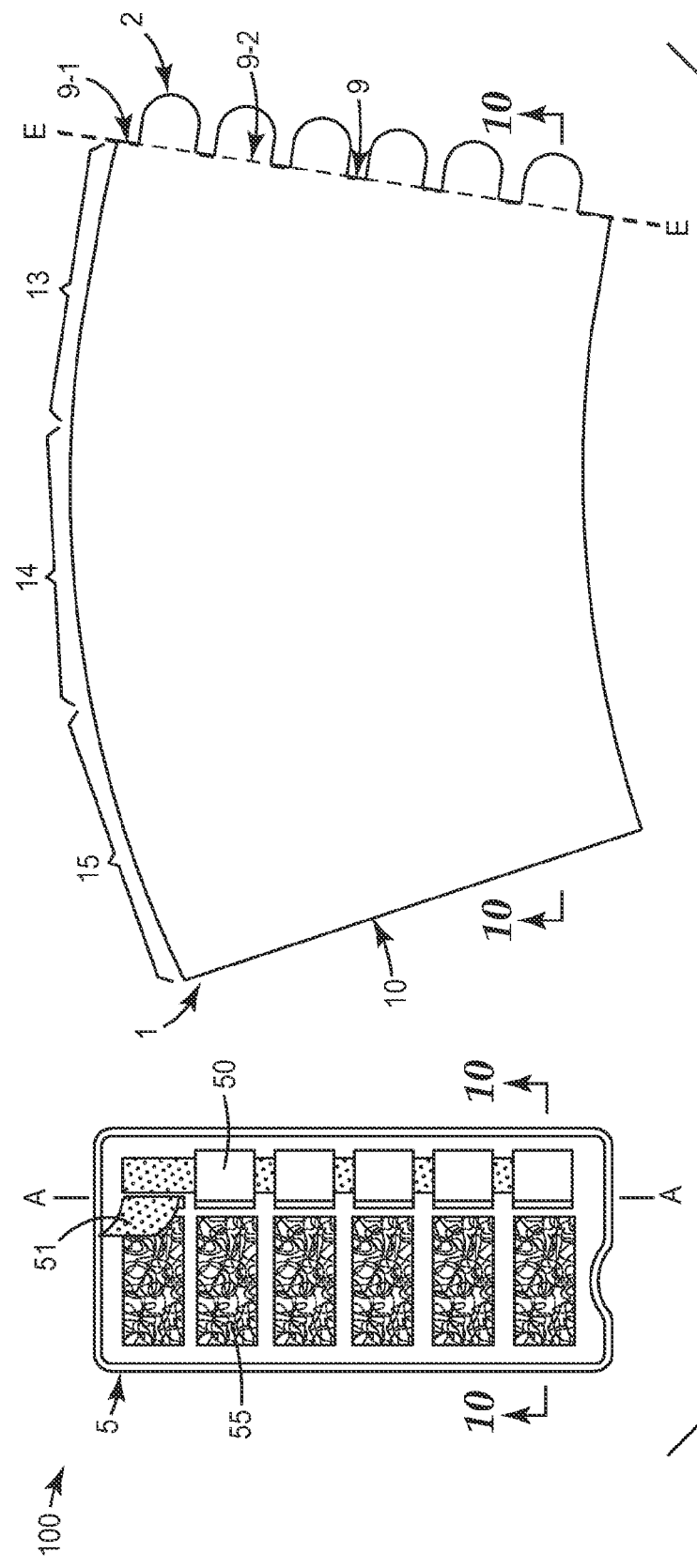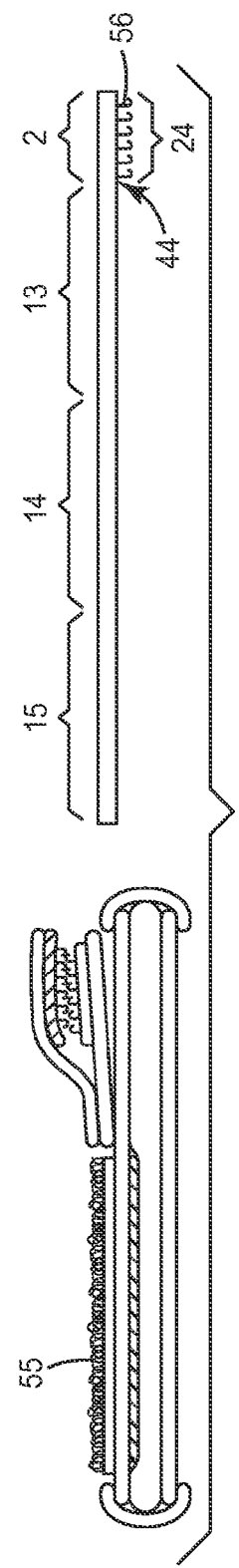

COMPRESSION DEVICE

Cross Reference to Related Applications

This application is a national stage filing under 35 U.S.C. 371 of PCT/US2015/050945,filed Sep. 18, 2015, which claims the benefit of Great Britain Application No. 1416782.9, filed Sep. 23, 2014, the disclosures of which are incorporated by reference in their entirety herein.

FIELD

The present invention relates to compression systems, in particular compression systems for applying compression to a body part (e.g. a limb, torso, neck or head) of a user for the use in the treatment and/or management of oedema and other venous and lymphatic disorders, more particularly venous leg ulcers and lymphoedema of a limb.

BACKGROUND

Compression therapy is generally prescribed to support an insufficient venous or lymphatic system in returning blood or lymph to the heart. Accordingly compression is generally considered to be the standard treatment for use in the treatment of oedema and other venous and lymphatic disorders e.g. of the lower limbs venous leg ulcers and other clinical conditions, such as lymphoedema. The positive effects of compression therapy on venous lymph return, as well as on the healing of chronic venous (leg) ulcers, are well documented in the medical literature.

Compression bandages are one of the common compression systems used for compression therapy. The use of such compression bandages generally involves the application of a multilayer compression bandage. One concept behind a number of such multi-layer bandaging systems is the use of a combination of different types of bandage layers in order to apply pressure in layers (giving an accumulation of pressure) and to provide sustained compression together with rigidity. Commercially available compression bandages include bandages marketed under the trade designations "3M COBAN 2" and "3M COBAN 2 LITE". Typically to assure proper and effective compression bandaging, it is normally necessary for a medical professional to apply the bandages. In consideration of the fact in the start of treatment of lymphoedema or in other compression therapies where oedema is present, compression bandages typically need to be replaced frequently due to changes in pressure (e.g. reduction of pressure) and/or in uniformity of pressure of the compression bandage as the amount of oedema is reduced during compression therapy, the need of having a medical professional change and reapply the compression bandage to ensure the desired pressure profile for continuing compression treatment can be limiting.

Compression stockings are often applied by users themselves. However they often do not provide the desired therapeutic compressive pressure or are alternatively very hard to put on. Moreover, compression stockings need to be quite elastic showing high stretch so that one can pull them on and off. Such stockings retain this high stretch while being worn on the limb, and accordingly their effectiveness in terms of compression therapy is rather limited.

Other compression systems have been marketed and/or proposed. For example, U.S. Pat. No. 6,152,893 (Pigg et al; SMITH& NEPHEW) discloses a compression device for applying a predetermined compression to a limb comprising a pliable non-extensible sheet to be wrapped around a limb, where said sheet is provided with a plurality of cooperating first and second fastening parts each along opposing edges of the sheet, thereby to secure the device to the limb, wherein said first fastening part is provided with a plurality of first and second related indicia that visually indicate the relative movement of said first fastening part relative to said second fastening part between the application of zero tension as indicated by said first indicia and the application of a predetermined optimal degree of tension as indicated by said second indicia on fastening said first and second parts to provide compression. WO 01/72250 (Bennet et al; NEOPRESS) discloses an elastic compression support for supporting a wound dressing around the lower leg and foot of a patient, the support comprising a panel and a line of fastenings for drawing together two long edges of the panel where the fastenings comprise mutually aligned pairs of tapes secured to or tabs integral with the panel along its edges arranged so that drawing the tape or tabs apart in mutually opposite directions causes the panel to be tightened in compression around the limb, wherein the panel is formed from three pieces including a central piece, that lies at the back of the calf and under the foot, made of a long-stretch microperforated neoprene and two side pieces, that form the two long edges of panel and lie along the shin and the front of the leg, made of short-stretch microperforated neoprene. WO 97/46181 (Shaw et al; CIRCAID MEDICAL PRODUCTS) discloses a therapeutic compression garment including a plurality of pairs of body or limb encircle bands integrally connected to a central wrap around region and extending outwardly in opposite direction from the both sides of the central region to encompass the body part. WO 2011/066237 (Lipshaw et al; CIRCAID MEDICAL PRODUCTS) discloses a therapeutic compression garment, including: a body portion; and a spine portion, wherein the spine portion is releasably attached along a spine curve onto the body portion such that the spine portion is positionable at different locations on the body portion and wherein there are bands extending from either the body portion and/or the spine portion, the bands further securing the body and spine portions together when the body and spine portions are wrapped around a body limb. A corresponding garment is marketed by CIRCAID under the trade designation JUXTA-CURES which is formed from the body and spine portion between attached over a spine curve and includes four limb encircling bands (two per side, each including hook & loop type fasteners) integrally connected to both the body portion and the spine portion, the bands being located in staggered positions along the two opposite sides garment and extending outwardly in opposite directions from the both sides of the garment to encompass the body part. US 2005/0209545 (Farrow et al; FARROW MEDICAL) discloses an apparatus for applying pressure to a body part comprising multiple interconnectable bands of compressible or non-compressible material and that the bands can be overlapped and connected to either via an spine or connective means lengthwise centrally in each band. A corresponding system is marketed by FARROW under the trade designation FARROWWRAP.

SUMMARY OF THE INVENTION

While the aforementioned other compression systems may be, in part, easier to put on, it has been found that these systems still suffer a number of disadvantages, e.g. not providing desirable therapeutic compressive pressure and/or showing open areas, e.g. between bands or other open spaces (leading to undesirable area(s) of non-compression within a region undergoing compression and thus a unfavorable potential for fluid accumulation in said area(s)) and/or wrinkling.

Accordingly there is an ongoing need or desire for a compression system that provides desirably effective compression therapy and is at the same time easy to put on and use, ideally without necessarily having a medical professional put it and/or change it each and every time.

We have found that it is particularly advantageous to provide a sleeve for substantially covering a portion of the body part (e.g. a limb, torso, neck, head) of a user where the sleeve is provided with a closure system, such that in use upon closure of the closure system the sleeve is restrained and tightened about the body part of the user to provide compression (e.g. by drawing together the lateral side edges of sleeve), where the main material of the sleeve serving to provide compression has particular, select material properties. In this regard it has been found to be particularly favorable to use a material having elasticity in the transverse direction and longitudinal direction of the sleeve together a maximum elongation from 5% to 35% under a load of 10 N per cm width in said transverse direction in conjunction with tension and elongation characteristics in at least one of said directions of the sleeve such that the initial slope of a tension-elongation curve, e.g. in that region below a force of 1 N/cm is not too steep.

Moreover, we have observed, although materials with very short stretch characteristics favorably facilitate effective compression therapy, e.g. facilitating the provision of desirably high standing pressures as a result of a high resistance to stretch, such materials, as a result of their high resistance to stretch, typically have issues in terms of surface conformability, which can lead to, among other things, gapping and/or wrinkling of the material and thus non-uniformity of compression. Surprisingly, we have found that the elongation characteristics at very low tension forces (below 1 N/cm) play a role here and that by purposively selecting a very short stretch material that has tension-elongation characteristic in at least one direction such that the initial slope in the tension-elongation curve is equal to or less than 0.9 N/(cm·%), one can facilitate the provision of advantageous favorable surface conformability even though the material is highly resistance to stretch and/or provides a high static (or dynamic) stiffness index.

Accordingly, in one aspect of the present invention there is provided a compression system for applying compression to a body part of a user comprising a sleeve for substantially covering a portion of the body part of a user, wherein the sleeve has two lateral side edges, wherein in the transverse direction from the first lateral side edge to the second lateral side edge the sleeve comprises a first lateral side region, a central region and a second lateral side region, wherein at least the central region of the sleeve comprises a material (main material) having elasticity in the transverse direction and longitudinal direction of the sleeve, said main material having a maximum elongation in said transverse direction of the sleeve from 5% up to and including 35% under a load of 10 N per cm width and having tension and elongation characteristics in one of said directions of the sleeve (first sleeve direction) such that the slope of a tension-elongation curve in that region of the curve where the force per cm width ranges from 0.1 N/cm to 0.9 N/cm is equal to or less than 0.9 N/(cm·%); the compression system further comprising a releasable closure system, said closure system being configured and arranged relative to the sleeve, such that, in use, upon closure of the closure system the sleeve is restrained and tightened about the body part of the user.

For the sake of clarity, it is to be appreciated that after application of a compression device onto a body part (e.g. a limb, torso, neck or head) of a user, the transverse direction of the sleeve will also be a circumferential direction. It is to be appreciated that releasable closure system may be provided as a part of the sleeve or as a separate component to the sleeve or a combination thereof, i.e. in part as a separate component and in part as part of the sleeve.

In accordance with ASTM D4848-98 (2012) and BS EN 14704-1:2005 elasticity is that property of a material by virtue of which it tends to recover its original size and shape immediately after removal of the force causing deformation. Elongation, recovered elongation as well as the tension-elongation characteristics may be determined in accordance with the standard BS EN 14704-1:2005 "Determination of the elasticity of fabrics,—Part 1: Strip tests": Method A, Knitted Fabrics e.g. as described in detail below in the experimental section. It will be appreciated that the given range of tension versus elongation slope—equal to or less than 0.9 N/(cm·%)—does not encompass an undefined slope, i.e. a vertical line, but does encompass a slope equal to zero N/(cm·%), i.e. horizontal line, although typically the slope will be greater than zero N/(cm·%). Moreover generally it is favorable that at least a minimal amount of initial resistance is given and accordingly the slope is favorably equal to or greater than 0.05 N/(cm·%).

To further facilitate surface conformability, desirably the main material has tension and elongation characteristics in said second sleeve direction, such that the slope of a tension-elongation curve in that region of the curve where the force per cm width ranges from 0.1 N/cm to 0.9 N/cm is equal to or less than 0.9 N/(cm·%).

To further facilitate effective compression, favorably main materials have a maximum elongation in the longitudinal direction under a load of 10 N per cm width from 5% up to and including 70%. In addition or alternatively thereto, favorably the sum of the maximum elongations of the main material in the transverse and longitudinal directions of the sleeve under a load of 10 N per cm width is in the range from 10% up to and including 75%.

In the event, a main material shows maximum elongation properties such that the direction of the main material (e.g. its machine direction or cross-web direction) may be oriented in either the transverse or longitudinal direction of the sleeve, favorably, sleeves are constructed such that the direction with the lowest initial tension-elongation slope is oriented along or essentially along the transverse direction of the sleeve. Ideally, this material direction also shows the lowest maximum elongation, which often holds true when the machine direction of the material is the direction having the lowest initial tension-elongation slope.

Main materials favorably have a recovered elongation in the transverse direction of the sleeve and/or in the longitudinal direction of the sleeve equal to or greater than 90%, in particular equal to or greater than 95%.

To facilitate wearing comfort, main materials favorably have from its inner surface to its outer surface and/or from its outer surface to its inner surface an air permeability of at least 20 cm/sec, in particular at least 60 cm/sec, more favorably at least 100 cm/sec, according to test ISO 9237-1995 using at a test pressure of 200 Pa. In addition or alternatively thereto, main materials favorably have from its inner surface to its outer surface a water vapor transmission rate equal to or greater than 1000 g/(m$^2$·24 h), more favorably equal to or greater than 1600 g/(m$^2$·24 h), even more favorably equal to or greater than 2200 g/(m$^2$·24 h), most favorably equal to or greater than 2800 g/(m²·24 h) as measured according to ISO 15106, part 1.

Compression systems are favorably configured and arranged such that the area of the central region is at least 40% (in particular at least 45%, more particularly at least 50%) of the total area of the sleeve. In addition or alternatively thereto, compression systems may be favorably configured and arranged such that at a height corresponding to two-thirds the height of sleeve, the central region of the sleeve extends 40% or more across the sleeve in its transverse direction. It will be appreciated that said height corresponding a "two-thirds height position" towards the torso of the wearer. For example for sleeves including a lower edge and upper edge, the latter positioned towards to the torso of the wearer in use, said height would correspond two-thirds the height of sleeve from the lower edge to the upper edge.

Favorably at least 85% (in particular at least 90%, more particularly at least 95%) of the total area of the central region of the sleeve is made of said main material.

It is to be appreciated that since compressions systems, in particular the sleeves thereof will expand and/or change form in use, the aforesaid percent areas and width are relative to respective areas and width in the device when it is not in use. Further, it is to be appreciated that the sleeve, in particular the central region thereof, may comprise or be made of a single material having the corresponding properties of a main material or alternatively one or more materials each having the corresponding properties of a main material e.g. provided in series along the transverse and/or longitudinal directions of the sleeve or alternatively one or more materials in the form of a composite material (e.g. laminate), said composite material having the corresponding properties of a main material.

As indicated above, compression systems described herein, in particular sleeves thereof, are particularly suited for covering a portion of a limb, a portion of the torso, a portion of the neck, a portion of a head or a portion of a neck and head in combination of a user e.g. for the use in the treatment and/or management of oedema.

The dependent claims define further embodiments of the invention.

It is to be understood that the present invention covers all combinations of particular, suitable, desirable, favorable advantageous and preferred aspects of the invention described herein.

BRIEF DESCRIPTION OF DRAWINGS

The invention will now be described with reference to the accompanying drawings in which:

FIG. 1 represents a top view of an exemplary embodiment of a compression system in accordance with the invention described herein, while FIG. 2 shows a cross-sectional view of a part (i.e. the secondary closure element) of the exemplary embodiment depicted in FIG. 1.

FIG. 3 represents perspective, front view of the exemplary embodiment depicted in FIG. 1 shown in a configuration corresponding to the embodiment being about a limb of a user (limb not shown) with the sleeve and secondary closure element being attached via the flaps and the fastening bands and wherein the sleeve is tightened about the limb to provide compression, while

FIG. 5 represents a top view of another exemplary embodiment of a compression system in accordance with the invention described herein, while FIG. 6 shows a cross-sectional view of a part (i.e. the sleeve element) of the exemplary embodiment depicted in FIG. 5.

FIG. 7 represents a top view of an additional exemplary embodiment of a compression system in accordance with the invention described herein, while FIG. 8 shows a cross-sectional view of a part (i.e. the sleeve element) of the exemplary embodiment depicted in FIG. 7.

FIG. 9 represents a top view of a further exemplary embodiment of a compression system in accordance with the invention described herein, while FIG. 10 shows a cross-sectional view of the exemplary embodiment depicted in FIG. 9.

FIG. 11 represents a front view of an exemplary test specimen being assessed for surface conformability according to a method described herein, while

Figure 3:
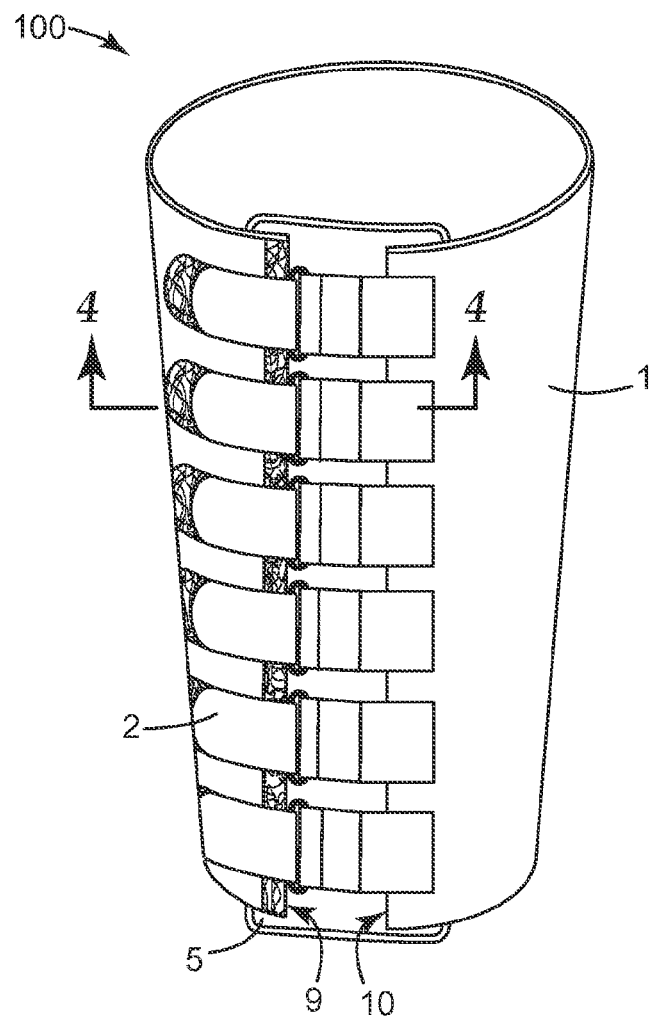

In the description that follows, unless expressly stated otherwise, terms such as 'top', 'bottom', 'above', 'below', etc, refer only to features as shown in the Figures, and no restriction as to orientation of use, etc, is intended. Not all Figures are to the same scale.

DETAILED DESCRIPTION

It is to be understood that the present invention covers all combinations of particular, suitable, desirable, favorable, advantageous and preferred aspects of the invention described herein.

FIG. 1 shows a top view of the exterior of an exemplary embodiment of a compression system (100) comprising a sleeve (1) for substantially covering a portion of the limb of a user and a secondary closure element (5), while FIG. 2 shows a cross-sectional view of the secondary closure element. As can be appreciated from FIG. 1, sleeves generally include an outer surface (3), an inner surface (4; not numbered on FIG. 1), an upper edge (7) and a lower edge (8). When the device is in use on the limb, typically the inner surface (4) is located towards the wearer/user (in the following the term "inner" will typically refer to something located towards the wearer/user and "outer" away from the wearer/user), while the upper edge is located towards to the torso of the user and the lower edge distant to the torso of the user, and both upper and lower edges, being essentially transverse, will be located essentially circumferentially around the limb after application. As mentioned above, after application of a compression device onto a body part (e.g. a limb) of a user, the transverse direction of the sleeve will essentially also be a circumferential direction. In FIG. 1, the symbols T← →T indicate the transverse direction of the sleeve while the symbols L← →L indicate the longitudinal direction of the sleeve. As can be appreciated from FIG. 1, the sleeve includes two lateral side edges (9, 10). In the transverse direction from the first lateral side edge (9) to the second lateral side edge (10) the sleeve comprises a first lateral side region (13), a central region (14) and a second lateral side region (15). The central region and the second lateral side region may structurally be the same as shown in the exemplary embodiment illustrated in FIG. 1. In alternative embodiments, the central region and the second lateral side region may be structurally different, for example as can be seen in the exemplary compression system (100) depicted in FIG. 5, where the outer surface (3) of the second lateral side region (15) of the sleeve (1) is provided with, in particular laminated to, an additional material layer (e.g. a loop engagement material) (28) having structure that can engage mechanical fastening elements (61) provided on the exterior flap (51) provided on the secondary closure element (5). See also FIG. 6, which provides a cross-sectional view of the sleeve in FIG. 5. In other alternative embodiments, the entire outer surface of the sleeve may be provided (e.g. laminated) with a material (e.g. a loop engagement material) having structure that can engage mechanical fastening elements. Returning to the exemplary embodiment depicted FIG. 1, it will be appreciated that since the central region and second lateral side region are structurally the same, there is no discernible boundary between the two regions. Having regard to the continuous region of the two, i.e. the joint-region, in the following the second lateral side region (15) will be generally understood to be the half of the joint-region that is adjacent to the second lateral side edge (10) while the central region will be generally understood to be the half of the joint-region adjacent to the first lateral side region. The second lateral side region (15) is free of structural elements like fastening bands or rings and thus is configured and arranged so that it can be trimmed, while the first lateral side region (13) of the sleeve is provided with a plurality of fastening bands (2) in series along substantially the longitudinal direction of the sleeve between the upper and lower edges of the sleeve, the bands being in this exemplary embodiment fixedly attached (e.g. sewn) to the outer surface at the first lateral side region of the sleeve.

Sleeves, when laid out flat for example as shown in FIG. 1, may be substantially rectangular, or substantially trapezoidal or irregular in shape. For example, the sleeves in exemplary embodiments depicted herein (e.g. in FIG. 1) are substantially trapezoidal in shape. For facilitating an optimal fit onto a part of the limb of a user, the upper edge and/or the lower edge of the sleeve may be favorably slightly curved, in particular the upper edge may be slightly convex and/or the lower edge which is normally positioned distant to the torso of the user, may be either slightly concave or convex. Alternatively or in addition thereto, one or both of the lateral side edges may be slightly curved, in particular slightly convex. This may be facilitating fitting over well-developed calves. In use, when the compression device is applied onto a limb of the user, favorably the sleeve is substantially cylindrical, barrel or truncated-conical in shape. It is to be noted that after use and removal of the compression system from the limb of a user the sleeve, when laid out, may not be perfectly flat.

Sleeves, in particularly the first and/or second lateral side regions thereof, may be provided with one or more stiffeners extending lengthwise to facilitate maintenance of sleeve shape and/or to improve local pressure distribution, in particular to minimize any tendency towards vertical collapsing or slipping-down of the sleeve, stiffeners may be provided e.g. in the form of wires, bars, grids, or pads having limited width relative to the transverse direction of the sleeve. For example, an elongate stiffener that extends lengthwise between the upper and lower edges of the sleeve could be provided in the first lateral side region, in particular adjacent to the first lateral edge. Stiffeners may be made of e.g. metal or thermoplastic materials including thermoformable thermoplastic materials (such as polypropylene, polyamide, polyester (e.g. 3M SCOTCHCAST™ Thermoplastic Material 72362)). For stiffeners having a width greater than five millimeters, it may be favorable to provide them with perforations to allow for breathability. For design and/or fixing purposes, stiffeners may be provided within a fabric pocket which is subsequently attached to the appropriate part(s) of the sleeve or alternatively stiffeners may be positioned on the surface of the appropriate part(s) of the sleeve, which are then covered completely with a sheet of fabric that is sewn or laminated onto the respective part(s) of the sleeve.

The provision of a trimmable second lateral side region facilitates the provision of good and individualized anatomic fit, which in turn facilitates the provision of the needed and/or desired compression for that particular user.

Compression systems described herein, in particular the sleeves thereof, can be provided in different sizes to accommodate the difference in the size of body parts (e.g. limbs versus torsos or necks or heads; or e.g. relative to just limbs, arms versus legs) as well as the general difference in sizes of a particular body part. Compression systems suitable for use with necks and heads will often be used for both, i.e. configured to cover a portion of both the neck and head of the user. Such devices may be configured for example like a hood covering the neck, chin and over the head leaving the face free where the releasable closure system may be provided either along the top and back of the head or along the front down the chin and front of the neck.

Compression systems described herein are particularly useful for applying compression to a limb. Desirably the sleeve is configured and arranged to cover a limb such that the sleeve extends over at least one major muscle of the limb. For example, for compression systems designed for use on a leg (e.g. the lower leg and/or the upper leg), said at least major muscle may be appropriately selected from the following: tibialis anterior, soleus, gastrocnemius, bicep femoris, rectus femoris, vastus medialis, vastus intermedius and vastus lateralis; while for compression devices designed for use on an arm (e.g. the lower arm and/or the upper arm) said at least major muscle may be appropriately selected from the following: flexor carpi radialis, flexor carpi ulnaris, palmaris longus, brachioradialis, biceps brachii, triceps brachii, and brachialis. Typically a combination of major muscles will be covered.

Sleeves of compression systems described herein can be provided in different sizes to accommodate the difference in the size of limbs (e.g. arms versus legs) as well as the general difference in sizes of a particular limb. Compression systems described herein are particularly suitable for use on the lower leg including the calf. In regard to the latter considering the length of an adult human lower leg can range from around 20 cm to 50 cm, it could be possible to provide, three height sizes, e.g. short, average and, tall, again aimed to cover 80% of the potential relevant lengths of the potential users. In addition and more significantly, considering the size of an adult human lower leg, including those persons suffering from lymphedema, can range from around 130 to 420 mm in circumference at the ankle and around from 280 to 650 mm in circumference at their widest point, it could be possible to provide compression systems in for example seven standard width sizes, e.g. XS, S; M, L, XL, XXL, XXXL, aimed to cover 80% of the potential relevant circumferential sizes of the potential users while the remaining 20% could be provided for by special order. The application of compression systems described herein where the second lateral side region of the sleeve is configured such that it is trimmable is also advantageous in that it allows for the reduction in the number of standard sizes to cover 80% the potential relevant circumferential sizes of the potential users. For example, instead of providing seven sizes one could provide three sizes corresponding in size to M, XL and XXXL indicated above, where then the width of the sleeve could be readily adjusted by the user or the care-giver applying the compression system onto the limb of the user to smaller sizes, e.g. XL down to L. In addition as mentioned above, in the event that the compression therapy is effective (as it should be) such that the circumference of the limb is significantly reduced, the width of the sleeve can be easily further re-adjusted by the user or the care-giver to even a smaller size, e.g. L to M. In the illustrated exemplary embodiment depicted in FIG. 1, the fastening bands are fixedly attached to the first lateral side region In order to facilitate a further degree of freedom or flexible as to sizing, especially having regard to the aforesaid "remaining 20%" that would normally needed to be provided for by special order, in alternative embodiments, the fastening bands may be releasably attachable to the first lateral side region of the sleeve, where then the first lateral side region of the sleeve may also be configured and arranged such that it is trimmable. For such embodiments, it can be envisioned that compression systems described herein may be favorably provided in a system including sleeve material, e.g. in a roll, with one or more sets including an appropriate series of the fastening bands and a secondary closure element.

For compression systems suitable for use with the lower leg of the user, favorably the sleeve is configured and arranged such that in use the central region of the sleeve will typically be positioned around the back and, at least on one of the sides of the lower leg, and thus accordingly next to the calf muscles.

Returning to the embodiment shown in FIG. 1, it will be noted that the three regions (13, 14, and 15) of the sleeve comprise the same material (30). This material is the main material. Further it should be appreciated due to the attachment of fastening tabs (2) at the first lateral side region (13), the properties of the underlying main material (30) in this region will normally be affected. Moreover the maximum elongation in the transverse direction under a load of 10 N per cm of the first lateral side region will typically be lower (most often significantly lower approaching and possibly reaching 0% elongation) than the maximum elongation in the transverse direction under a load of 10 N per cm of the central region of the sleeve. Finally it will be appreciated that in the central region of the sleeve, this region being free of such attachments, the properties of the main material remain un-affected.

As indicated above, at least the central region of the sleeve comprises a material (i.e. main material) having elasticity in the transverse direction and longitudinal direction of the sleeve, having a maximum elongation in said transverse direction of the sleeve from 5% up to and including 35% under a load of 10 N per cm width and having tension and elongation characteristics in one of said directions of the sleeve (first sleeve direction) such that the slope of a tension-elongation curve in that region of the curve where the force per cm width ranges from 0.1 N/cm to 0.9 N/cm is equal to or less than 0.9 N/(cm·%). Desirably the main material has tension and elongation characteristics in said second sleeve direction, such that the slope of a tension-elongation curve in that region of the curve where the force per cm width ranges from 0.1 N/cm to 0.9 N/cm is equal to or less than 0.9 N/(cm·%).

Favorably, the main material has tension and elongation characteristics in said first sleeve direction such that said slope of tension versus elongation curve is equal to or less than 0.75 N/(cm·%), more favorably equal to or less than 0.50 N/(cm·%), most favorably equal to or less than 0.3 N/(cm·%). In addition or alternatively thereto, favorably the main material has tension and elongation characteristics in said second sleeve direction such that said slope of tension versus elongation curve is equal to or less than 0.75 N/(cm·%), more favorably equal to or less than 0.50 N/(cm·%), most favorably equal to or less than 0.3 N/(cm·%).

Favorably the main material has a maximum elongation in said transverse direction from equal to or less than 33% under a load of 10 N per cm width, more favorably equal to or less than 30% under a load of 10 N per cm width. Favorably main materials have a maximum elongation in said transverse direction from equal to or greater than 6% under a load of 10 N per cm width, more favorably equal to or greater than 7% under a load of 10 N per cm width.

Favorably main materials have a maximum elongation in the longitudinal direction under a load of 10 N per cm width from 5% up to and including 70%. More favorably such materials have a maximum elongation in the longitudinal direction under a load of 10 N per cm width equal to or less than 55%, most favorably equal to or less than 45%. In addition or alternatively, such materials more favorably have a maximum elongation in the longitudinal direction under a load of 10 N per cm width equal to or greater than 7%, in particular equal to or greater than 12%.

Favorably the sum of the maximum elongations of the main material in the transverse and longitudinal directions of the sleeve under a load of 10 N per cm width is in the range from 10% up to and including 75%. More favorably the sum of the maximum elongations of the main material in the transverse and longitudinal directions of the sleeve under a load of 10 N per cm width is equal to or less than 70%, most favorably equal to or less than 65%. In addition or alternatively thereof, the sum of the maximum elongations of the main material in the transverse and longitudinal directions of the sleeve under a load of 10 N per cm width is more favorably equal to or greater than 14%, most favorably equal to or greater than 19%.

Main materials favorably have a recovered elongation in the transverse direction of the sleeve and/or in the longitudinal direction of the sleeve equal to or greater than 90%, in particular equal to or greater than 95%.

Desirably main materials are rather flexible to facilitate application as well as general fitting of the sleeve onto the relevant portion of the body part (e.g. limb, torso, neck, or head). Favorably main materials show a bending length in the transverse and/or the longitudinal direction equal to or less than 20 cm, in particular equal to or less than 15 cm; more particularly equal to or less than 10 cm, most particularly equal to or less than 5.0 cm. Alternatively or in addition, favorably main materials show a flexural rigidity in the transverse and/or the longitudinal direction equal to or less than 150 mN·cm, in particular equal to or less than 125 mN·cm; more particularly equal to or less than 75 mN·cm, most particularly equal to or less than 35 mN·cm. The bending length and flexural rigidity of fabrics may be determined according to ISO 9073-7 1$^{st}$ Edition 1995-12-15 "Textiles—Test methods for nonwovens Part 7: Determination of bending length" or ASTM D1388-08 "Standard Test Method for Stiffness of Fabrics", using e.g. M003B Shirley Stiffness Tester and pre-conditioning specimens (each cut relative to particular direction to be measured to 1 inch×8 inch (i.e. 25.4 mm×203.2 mm)) for 24 hours and tested at 21° C. and 65% RH.

To facilitate wearing comfort, main materials favorably have from its inner surface to its outer surface and/or from its outer surface to its inner surface an air permeability of at least 20 cm/sec, in particular at least 60 cm/sec, more favorably at least 100 cm/sec, according to test ISO 9237-1995 using at a test pressure of 200 Pa. In addition or alternatively thereto, main materials favorably have from its inner surface to its outer surface a water vapor transmission rate equal to or greater than 1000 g/(m$^2$×24 h), more favorably equal to or greater than 1600 g/(m$^2$·24 h), even more favorably equal to or greater than 2200 g/(m$^2$·24 h), most favorably equal to or greater than 2800 g/(m$^2$·24 h) as measured according to ISO 15106, part 1.

Main materials may favorably comprise foam, e.g. in the form of a laminate where one or both major surfaces are provided with a fibrous fabric (e.g. a woven, knitted, nonwoven or felt textile or cloth). For certain embodiments where hook-type fasteners are employed in the releasable closure system of the compression system, discussed in more detail below, the fabric may favorably have a hook-engageable surface.

Favorably main materials comprise a fibrous fabric, in particular a woven or knitted fabric, more particularly a knitted spacer fabric. Knitted spacer fabrics are three-dimensional knitted fabrics having two knitted substrates (e.g. a top layer and a bottom layer) which are joined together by spacer yarns (as an intermediate connecting layer). Favorably for the facilitation of overall robustness of such fabrics, in particular knitted spacer fabrics, have a basis weight equal to or greater than 100 g/m$^2$, more favorably equal to or greater than 150 g/m$^2$, even more favorably equal to or greater than 200 g/m$^2$, most favorably equal to or greater than 250 g/m$^2$. In addition or alternatively thereto, to allow for and/or to facilitate a cushioning effect such fabrics, in particular knitted spacer fabrics, desirably have a thickness equal to or greater than 0.5 mm, more desirably equal to or greater than 1.0 mm, even more desirably equal to or greater than 1.4 mm, and most desirably equal to or greater than 1.8 mm. In addition or alternatively thereto, to generally facilitate breathability and/or permeability of such fabrics, in particular knitted spacer fabrics, desirably have a thickness equal to or less than 6.0 mm, more desirably equal to or less than 5.2 mm, even more desirably equal to or less than 4.4 mm, and most desirably equal to or less than 4.0 mm. Warp knitted spacer fabrics have been found to be particularly suitable. Warp-knitted spacer fabrics are typically knitted on a rib Raschel machine having two needle bars. An example of a suitable warp-knitted spacer fabric includes the spacer fabric marketed by Akkotex; Via dell'Impresa, 20; 36040 Brendola (Vicenza), Italy under the designation as Rete Big Hole, Nero. Such fabrics, in particular knitted spacer fabrics, may be used as is or alternatively used in a form of a laminate, where one or both major surfaces are provided with a second (or third as the case may be) fibrous fabric (e.g. a woven, knitted, nonwoven or felt textile or cloth). Again for certain embodiments where hook-type fasteners are employed in the releasable closure system of the compression system, the second (or third) fabric may favorably have a hook-engageable surface. Examples of fabrics providing hook-engageable surface include so-called unbroken loop (UBL) materials for example like those marketed by Gehring Textiles Inc., Garden City, N.Y. 11530, USA under the product numbers WW983 and WW1306. Examples of suitable laminates include a two layer laminates of the aforementioned WW983 UBL material with the warp knitted spacer fabric marketed by Gehring Textiles Inc., Garden City, N.Y. 11530, USA under the trade designation SHR 700/3 D3 D/0 7208810 and the warp spacer fabric marketed by Müller Textil, 51674 Wiehl, Germany under the trade designation 3 Mesh 7808.

Favorably main materials have basis weight equal to or greater than 100 g/m$^2$, more favorably equal to or greater than 150 g/m$^2$, even more favorably equal to or greater than 200 g/m$^2$, most favorably equal to or greater than 250 g/m$^2$. In addition or alternatively main materials favorably have basis weight equal to or less than 550 g/m$^2$.

Favorably main materials have a thickness equal to or greater than 0.5 mm, more desirably equal to or greater than 1.0 mm, even more desirably equal to or greater than 1.4 mm, and most desirably equal to or greater than 1.8 mm. In addition or alternatively thereto, such fabrics, in particular knitted spacer fabrics, desirably have a thickness equal to or less than 6.0 mm, more desirably equal to or less than 5.2 mm, most desirably equal to or less than 4.4 mm.

To minimize or avoid creation of impressions on the skin and/or a potential of skin irritation, in the event a compression system is worn without any stockings, favorably fabrics, in particular knitted spacer fabrics, do not have large open patterns on the side of the fabric that will be facing the skin; desirably at least in one direction (e.g. machine or cross direction) the breadth of opening(s) is equal to or less than 3 mm. In the other direction (e.g. cross or machine direction, respectively) the breadth may be equal to or less than 3 mm or alternatively greater than 3 mm.

Compression devices are favorably configured and arranged such that the area of the central region is at least 40% (in particular at least 45%, more particularly at least 50%) of the total area of the sleeve (when the device is not in use). In addition or alternatively thereto, compression devices may be favorably configured and arranged such that at a height corresponding to two-thirds the height of sleeve, for example from its lower edge to its upper edge if applicable, the central region of the sleeve extends 40% or more across the sleeve in its transverse direction (when the device is not in use).

Favorably at least 85% (in particular at least 90%, more particularly at least 95%) of the total area of the central region of the sleeve is made of said main material (when the device is not use).

In the event the first and/or second lateral side regions include the same material as the central region, said material having the corresponding properties of a main material, due to the provision of the respective parts of the releasable closure system, attachment of an optional tongue and/or stiffeners generally the respective regions may not have the corresponding properties of a main material, where typically the maximum elongation in the transverse direction under a load of 10 N per cm of will be lower (most often significantly lower approaching and possibly reaching 0% elongation) than the maximum elongation in the transverse direction under a load of 10 N per cm of the central region of the sleeve. In the event, the first and/or second lateral side regions do not comprise main material, but another material or materials, again relative to the device as a whole including the releasable closure system elements and/or other elements provided on the first and/or second lateral side regions, desirably the first and second lateral side regions are not more stretchable in the transverse direction than the central region. Moreover desirably the first lateral side region and the second lateral side region show a maximum elongation in the transverse direction under a load of 10 N per cm that is equal to or less than the maximum elongation in the transverse direction under a load of 10 N per cm in the central region of the sleeve. In addition or alternatively thereof, the first lateral side region and the second lateral side region may show a maximum elongation in the longitudinal direction under a load of 10 N per cm that is equal to or less than the maximum elongation in the longitudinal direction under a load of 10 N per cm in the central region of the sleeve.

Compression systems described herein further comprise a releasable closure system. The closure system is configured and arranged relative to the sleeve, such that, in use, upon closure of the closure system the sleeve is restrained and tightened about the body part (e.g. limb, torso, neck or head) of the user. Desirably the sleeve and closure system are configured and arranged such that in use, upon closure of the closure system, the two lateral edges of the sleeve are drawn towards one another, but do not overlap.

Releasable closure systems may include zippers, e.g. wherein the first lateral edge of the sleeve may be provided (releasably or fixedly) with one half of said zipper and the second lateral edge is provided (releasably or fixedly) with a complementary half of said zipper. The term "zipper" as used herein includes mechanical closure devices comprising two zipper-tape halves, each provided teeth or other elements including (e.g. male and/or female) interlocking profiles, which can interlocked together or disengaged from another via the use of a slider to form a closed or opened zipper chain, respectively. An example of a toothless zipper includes the closure system marketed by GORE under the trade designation LOCKOUT which includes a slider that interlocks the two double channeled polymer tracks.

Desirably releasable closure systems allow for individualized tightening along the longitudinal direction of the sleeve. Examples of such systems may include closure systems comprising a plurality of opposing lace guides provided on the outer surface of two lateral side regions of the sleeve and a lace extending back and forth between the opposed guides. Such closure systems may further comprise at least one rotatable tightening mechanism configured to apply tension on the lace thereby advancing the opposed guides towards each other. In particular the at least one rotatable tightening mechanism may be integrally formed with at least one guide. Typically in such reel-lacing systems the lace has no free end.

Other examples of such releasable closure systems may comprise a mechanical fastening closure system.

For example, the first lateral side region or the second lateral side region or both regions may be provided is provided with a plurality of fastening bands in series along substantially the longitudinal direction of the sleeve. Fastening bands may be integral with the respective lateral side region of the sleeve such that fastening bands extending in substantially the transverse direction of the sleeve out from the respective lateral side edge of the sleeve. Or fastening bands may comprise a proximal end portion, said proximal end portion being releasably or fixedly attached to the respective lateral side region of the sleeve such that the bands extends substantially the transverse direction of the sleeve over the respective lateral side edge. It will be appreciated that each fastening band has a first major surface and a second major surface, the first major surface facing inwardly and the second major surface facing outwardly.

Fastening bands typically comprise a distal end portion. Each band extends favorably in substantially the transverse direction of the sleeve with its distal end portion positioned away from the central portion of the sleeve. At least the distal end portions of the fastening bands may favorably have a height relative to the transverse direction of the sleeve of at least 1 cm, more favorably at least 2 cm, most favorably at least 3 cm. At least the distal end portions of the fastening bands may favorably have a height relative to the transverse direction of the sleeve of at most 10 cm, more favorably at most 8 cm, most favorably at most 6 cm.

Distal end portions of the fastening bands may advantageously comprise mechanical fastening elements (referred to in the following as first band fastening elements), in particular male fastening elements, more particularly male fastening elements selected from the group consisting of hook fasteners, mushroom-shaped fasteners, stem-shaped fasteners, cup-shaped fasteners, T-shaped fasteners, pin-shaped fasteners and mixtures thereof.

In one favored arrangement, mechanical fastening elements are provided on the first major surface at the distal end portion of the fastening bands, said fastening bands being provided on the first and/or second lateral side regions. The opposite second and/or first lateral edge regions may then favorably comprise a complementary engaging structure. For example the region(s), in particular its (their) outer surface, may have a structure or be provided (either releasably or fixedly) with a structure that is adapted to be engaged by said fastening elements.

Another example of a releasable closure system comprising a mechanical fastening closure system and favorably allowing for individualized tighten along the longitudinal direction of the sleeve includes systems including fastening bands in conjunction with rings. It will be appreciated that rings may be made of metallic or polymeric material or may be created or provided in a web material (e.g. in the form of an eyelet); they may be rectangular or substantially rectangular in form; or oval or substantially oval in form (e.g. narrow or elongate oval, canoe-form, elongate teardrop); or an elongate or narrow D-shape in form. In such favored arrangements, mechanical fastening elements may be provided on the second major surface at the distal end portion of the fastening bands provided on the first and/or second lateral side regions. For such embodiments the opposite second and/or first lateral edge regions may then be favorably provided (either releasably or fixedly) with a series of rings, such that there is a ring located opposite to a fastening band. In particular, the fastening bands and rings are configured and arranged such that, in use the bands are passed through the rings then turned back on themselves, such that the respective lateral side edge(s) of the sleeve is drawn towards the rings on the opposing lateral side region(s) and thus sleeve is tightened about the body part (e.g. limb, torso, neck or head) of the user, and then the fastening bands are fastened so that the sleeve is restrained about the body part of the user, more particularly one lateral edge is drawn towards the other lateral edge of the sleeve, but the two lateral edges of the sleeve do not overlap.

To allow for releasable fastening of the fastening bands, favorably first and/or second lateral side regions (i.e. the same region or regions provided with the fastening bands) comprise a complementary engaging structure. For example, the respective lateral side region(s) of the sleeve, in particular its (their) outer surface may have a structure or be provided (either releasably or fixedly) with a structure that is adapted to be engaged by the mechanical fastening elements on the second major surface of the distal end portion of the fastening bands. In addition or alternatively thereof, for those embodiments where the fastening bands comprise a proximal end portion that is (releasably or fixedly) attached to the outer surface of the respective lateral side region of the sleeve and the second major surface at the proximal end portion of the band may have a structure or be provided with a structure that is adapted to be engaged by the mechanical fastening elements on the second major surface of the distal end portion of the fastening bands.

The part of the fastening bands extending beyond the first and/or second lateral side edge may have a width relative to the transverse direction of the sleeve of at least 3 cm, in particular at least 6 cm. In addition or alternatively, the part of the fastening bands extending beyond the first lateral side edge generally has a width relative to the transverse direction of the sleeve of at most 25 cm. For those embodiments including fastening bands including proximal end portions, said proximal end portions may be connected and/or integral to one another.

As mentioned above for those embodiments including fastening bands including proximal end portions, the proximal end portion may be either fixedly or releasably attached to the respective first and/or second lateral side region of the sleeve. When they are releasably attached, first (inner) major surface at the proximal end portion may advantageously comprise mechanical fastening elements, in particular male fastening elements (second band fastening elements), more particularly male fastening elements selected from the group consisting of hook fasteners, mushroom-shaped fasteners, stem-shaped fasteners, cup-shaped fasteners, T-shaped fasteners, pin-shaped fasteners and mixtures thereof. In addition the outer surface of the respective first and/or second lateral edge region of the sleeve may have a structure or be provided with a structure that is adapted to be engaged by said second fastening elements. The second band fastening elements may be identical or different to fastening elements favorably provided at the distal end portions of fastening bands (first band fastening elements). It will be appreciated depending on the particular configuration it may be desirable to provide fastening elements, where the force for disengagement between the respective engaging structure and the second band fastening elements is higher (i.e. higher peel strength) than the force required for disengagement between the respective engaging structure and first band fastening elements.

For favorable embodiments where the second lateral side region is configured to be trimmable, it will be appreciated that if second lateral side region is to be provided with fastening bands, desirably they are configured and arranged such that they are releasably attachable to the second lateral side region, and in this manner they can be detached, and then after the region trimmed to size and fastening bands can be then re-attached. More favorably for such embodiments, where the second lateral side region is configured to be trimmable and the system includes fastening bands, it is advantageous to provide fastening bands only on the first lateral side region.

Returning to the exemplary embodiment depicted in FIGS. 1 and 2, it can be seen that the second lateral side region (15) of the sleeve is free of structural elements such as fastening bands and rings, and can be trimmed. As mentioned above the exemplary embodiment favorably includes a secondary closure element (5). This element is favorably configured as a tongue and is two-fold releasably attachable to the sleeve (1), i.e. to the fastening bands (2) provided in the first lateral side region (13) of the sleeve and to the second lateral side region (15) of the sleeve, in particular along the second lateral side edge (10). In particular it can be seen in FIG. 1, that the secondary closure element (5) of the compression system is favorably provided with a plurality of rings (16) in series lengthwise between the upper and lower edges (77, 88) of the closure element. There is a single ring provided for each of the fastening bands, such that when the closure element is (releasably) attached to the sleeve e.g. along the second lateral side edge (10), there is a ring located opposite to each of the fastening bands. In particular, the fastening bands (2) and rings (16) are configured and arranged such that, in use the bands can be passed through the rings then turned back on themselves, such that the first lateral side edge (9) of the sleeve (1) is drawn towards the rings and thus sleeve is tightened about the limb of the use, and then the fastening bands fastened so that the sleeve is restrained about the limb of the user, more particularly the first lateral edge is drawn towards the second lateral edge (10) of the sleeve, but the two lateral edges of the sleeve do not overlap.

In addition the closure element (5) is provided with a plurality of pairs of flaps (50) extending lengthwise in series to one side of the series of rings (16). In alternative embodiments, the closure element may be provided with a single elongate pair of flaps extending lengthwise to one side of the series of rings; such an exemplary embodiment is illustrated in FIG. 5 wherein the secondary closure element (5) is provided with a single elongate pair of flaps (50) extending lengthwise to one side of the series of rings (16) rather than a series of such pairs. Each pair of flaps includes an exterior flap (51) overlying an interior flap (52). As can be seen in the exemplary embodiment of FIG. 1, the interior flap of each of the pair of flaps is bridged and integral to the interior flap(s) of the neighboring pair(s) so that the interior flaps are provided in a form from a single elongate strip. It will be appreciated that the interior flaps can be alternatively provided in the form of a series of individual, separate (shorter) strips, like the exterior flaps. As can be appreciated from the embodiment shown FIG. 1, in particular from the cross-sectional view in FIG. 2, the opposing inner surfaces of the exterior and interior flaps (51, 52) comprise mechanical fastening elements (61, 62); said mechanical fastening elements (61, 62) being adapted to releasably engage the outer and inner surfaces (3, 4) respectively, of at least the second lateral side region (15) of the sleeve (1). It will be appreciated that each of the inner and outer surfaces of at least the second lateral side region of the sleeve may have a structure (e.g. integral to the particular material used for the sleeve) or may be provided with a structure (e.g. lamination of a second engaging material on the underlying material used for the sleeve) that is adapted to be engaged by mechanical fastening elements provided on inner surface of the interior and exterior flaps, respectively. Furthermore for each pair of flaps, at least the exterior flap (51) is movable relative to the interior flap (52) such that the exterior flap is capable of performing a hinge movement about a longitudinal or substantially longitudinal axis (A) and relative to the interior flap. This can be best seen in FIG. 1 to the upper left; here one of the exterior flaps is shown in an open position where in a hinged movement along the axis (A) the exterior flap is moved away from the interior flap and thus exposing its inner surface and mechanical fastening elements. The axis (A) for hinged movement of the exterior flap(s) (51) is positioned towards (proximal) to the series of rings (16). It can be seen that favorably the series of rings (16) are configured and arranged such that in use in when the closure element (5) is attached to the sleeve along the second lateral side edge (10) of the sleeve (1), the series of rings will be located distal the second lateral side edge.

The following provides an exemplary way of applying a compression system depicted in FIGS. 1 and 2 of a similar compression system including a secondary closure element: Desirably, the secondary closure element is preliminarily attached to the sleeve via the bands at a position which will allow for tightening in a later step. In other words, the fastening bands (2) are fastened in conjunction with secondary closure element (5), (e.g. using the opposing rings (16) on the closure element) thereby attaching the secondary closure element to along the first lateral side edge (9) of the sleeve (1) via the bands. Either before or thereafter, each of the exterior flaps (51) is moved in a hinge-movement away from the underlying interior flap (52) thereby exposing the inner surface and mechanical fastening elements (62) thereon. The secondary closure element (5) of the compression system (100) is positioned along the body part (e.g. a limb) of the user to be treated and the sleeve (1) is wrapped around the body part moving generally from the attached side of the sleeve to the unattached side, where a part of the sleeve (e.g. a part of the second lateral side region (15)) is placed over the inner surface of the interior flap(s) (52) on the secondary closure element so that the sleeve covers the body part in a selected manner and fit and such that the inner surface of the sleeve releasably engages with the mechanical fastening elements provided on the inner surface of the interior flap(s). In the event there is any excess and unengaged material of the sleeve (1) extending beyond the inner surface (as typically expected), in particular beyond the mechanical fastening elements of the interior flap(s) distal to the central portion of the sleeve, this is trimmed off e.g. with a pair of scissors. After trimming, or alternatively if the sleeve is by chance just the correct size, the inner surface (4) of that portion of the sleeve (1) that is adjacent to the second lateral side edge (10) (either newly created upon trimming or the original one) is engaged with the mechanical fastening elements (62) of the interior flap(s) (52), while at this point the exterior flaps (51) are still hinged away the interior flap(s), the mechanical fastening elements (61) of the exterior flaps being thus un-engaged. In a next step, the exterior flaps (51) are placed into contact with the outer surface (3) of the sleeve (1), e.g. via a hinged movement along the longitudinal axis L toward the interior flap(s) (52), so that the mechanical fastening elements (61) provided on the inner surface of the exterior flaps releasably engage the outer surface of the sleeve, in particular the outer surface of the portion of the sleeve whose inner surface (4) is releasably engaged with the fastening elements (62) of the interior flap (52). Once the system has been applied about the limb and properly sized as described, favorably the method includes the steps, un-fastening the fastening bands; repositioning to the fastening bands so as to tighten the sleeve about the limb of the user and provide a selected level of compression; and re-fastening the fastening bands.

It will be appreciated from the aforesaid description that the secondary closure element is configured and arranged relative to the sleeve such that, in use when the closure element is attached to the sleeve along the second lateral side edge and the fastening bands fastened, the closure element is generally centrally positioned adjacent to and extends along the first and second lateral side edges of the sleeve, so that the closure element is located between the user and an opening defined between the first and second lateral edges of the sleeve.

Figure 4:
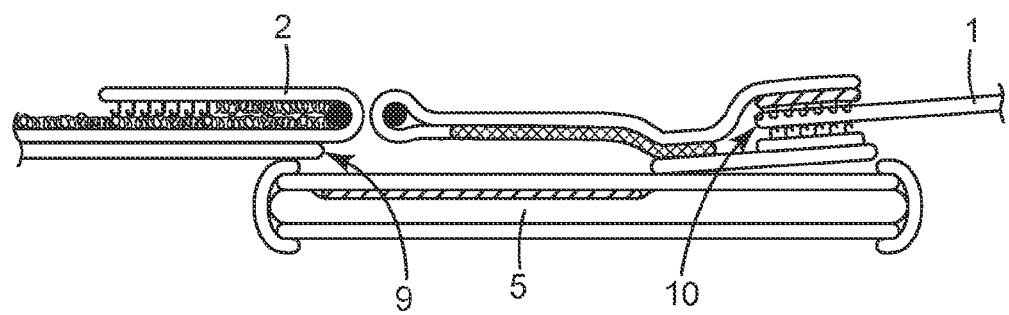
FIG. 4 shows a partial cross-sectional view of the exemplary embodiment in the configuration depicted in FIG. 3.

This is best recognized for example by reference to FIG. 3, which shows the exemplary compression system (100) of FIGS. 1 and 2 as it would look wrapped and tightened about e.g. a limb (limb not shown in FIG. 3) of a wearer. FIG. 4 shows a cross-sectional view of part of the exemplary embodiment in the configuration depicted in FIG. 3, from which is can be appreciated that the secondary closure element (5) is generally centrally positioned adjacent to and extends along the first and second lateral side edges (9,10) of the sleeve (1).

Referring to the cross-sectional view shown in FIG. 2, it can be recognized that each exterior flap (51) is affixed (in particular indirectly affixed) to the outer surface of the closure element (5) along the axis for hinged movement. It can also be recognized that the elongate strip forming the interior flaps is also affixed (in particular directly affixed) to the outer surface of the closure along the said axis for hinged movement. In alternative embodiment, the interior flap(s) may be completely affixed onto the outer surface of the closure element.

Generally, the mechanical fastening elements provided on the inner surfaces of the flaps favorably comprise male fastening elements, more favorably male fastening elements selected from the group consisting of hook fasteners, mushroom-shaped fasteners, stem-shaped fasteners, cup-shaped fasteners, T-shaped fasteners, pin-shaped fasteners and mixtures thereof (referred to in the following as flap fasteners or more specifically interior and exterior flap fasteners). The interior band fasteners may be identical to the exterior band fasteners or different. Similarly the structure of or provided on the inner surface of the sleeve may be identical to the structure of or provided on the outer surface of the sleeve.

It has been found desirable to configure and arrange the inner surface of the second lateral side region of the sleeve and the mechanical fastening elements of the inner surface of the interior flap so as to provide shear strength of at least 2 N/cm$^2$ as measured according to EN13780. In addition or alternatively, it has been found desirable to configure and arrange the inner surface of the second lateral side region of the sleeve and the mechanical fastening elements of the inner surface of the interior flap so as to provide peel strength less than 0.6 N/cm, more favorably equal to or less than 0.3 N/cm, as measured according to EN 12242. Examples of mechanical fastening elements tapes that may be suitable for use on the inner surface of the interior flap include low profile, extruded flexible film fastener tapes having mushrooms as engaging elements, such as those marketed by Gottlieb Binder GmbH & Co KG under the trade designation MICROPLAST, e.g. item nos. 25442, 25443, 25445, 25446 and 27443 or those marketed by 3M Deutschland GmbH (health care business) under the product number #7334.

It has been found desirable to configure and arrange the outer surface of the second lateral side region of the sleeve and the mechanical fastening elements of the inner surface of the exterior flap so as to provide shear strength of at least 7 N/cm$^2$ as measured according to EN13780. In addition or alternatively, it has been found desirable to configure and arrange the inner surface of the second lateral side region of the sleeve and the mechanical fastening elements of the inner surface of the interior flap so as to provide peel strength so as to provide a peel strength of at least 0.6 N/cm as measured according to EN 12242. In addition or alternatively, it has been found desirable to configure and arrange the inner surface of the second lateral side region of the sleeve and the mechanical fastening elements of the inner surface of the interior flap so as to provide peel strength so as to provide a peel strength of at most 10 N/cm, more desirably at most 5 N/cm, as measured according to EN 12242. Examples of mechanical fastening elements tapes that may be suitable for use on the inner surface of the exterior flap include woven mushroom tapes marketed by Velcro USA Inc. under the trade designation VELCRO (e.g. hook 088) or VEL-LOC or SUPER VEL-LOC (e.g. items 085, 083 or quadrilobal) or extruded hook tapes marketed by Alfatex Ltd. under the trade designation GRIPPER (e.g. medium pp).

Secondary closure elements, in particular secondary closure elements configured in the form of a tongue, may favorably include one or more elongate stiffeners extending lengthwise. As mentioned above, stiffeners may be made of e.g. metal or thermoplastic materials including thermoformable thermoplastic materials (such as polypropylene, polyamide, polyester (e.g. 3M Scotchcast Thermoplastic Material 72362)). For stiffeners having a width greater than five millimeters, it may be favorable to provide them with perforations to allow for breathability. For design and/or fixing purposes, stiffeners may be positioned on the surface of the appropriate part(s) of the closure element, which are then covered completely with a sheet of fabric that is sewn or laminated onto the respective part(s) of the closure element.

Secondary closure elements may comprise a spacer fabric and/or a foam material. Moreover the closure element comprises a multilayer construction comprising at least one layer, in particular two or more layers, of a material selected from the group consisting of a spacer fabrics, foams or combinations thereof. Suitable foams include memory foams, in particular high density memory foam. High density memory foams are memory foams that have a density of at least 65 kg/m$^3$, in particular at least 70 kg/m$^3$, more particularly at least 85 kg/m$^3$, most particularly at least 105 kg/m$^3$. Examples of suitable memory foams, include high density memory foams available from Filtrona Porous Technologies GmbH marketed under the trade designations SRF EP2, Argus, Argus Soft, and Argus Supersoft. Examples of suitable spacer fabrics include polyester spacer fabrics available from Müller Textil GmbH, 51674 Wiehl-Drabenderhöhe, Germany marketed under the product numbers 5754 and 6018. Closure elements, excluding structural elements attached thereto (e.g. flaps, rings, etc.), favorably have a thickness from 2 mm to 12 mm, inclusive, in particular a thickness from 3 mm to 8 mm, inclusive. In a region free of seams, stiffeners, if applicable, and attached structural elements (e.g. flaps, rings, etc), closure elements favorably have an air permeability equal to or greater than 40 cm/s, more favorably equal to or greater than 80 cm/s, even more favorably equal to or greater than 120 cm/s, most favorably equal to or greater than 160 cm/s, as measured according to ISO 9237:1995 using a test pressure of 200 Pa and/or a water vapor transmission rate equal to or greater than 1000 g/(m$^2$× 24 h), more favorably equal to or greater than 1600 g/(m$^2$× 24 h), even more favorably equal to or greater than 2200 g/(m$^2$×24 h), most favorably equal to or greater than 2800 g/(m$^2$×24 h), as measured according to ISO 15106, part 1.

Returning to the exemplary embodiment depicted in FIG. 1 and the cross-sectional view of the closure element in FIG. 2, it can be seen, that the closure element (5) includes an elongate stiffener (42) extending lengthwise. Desirably the elongate stiffener is positioned on the opposite side of the secondary closure element as the flaps, in other words the elongate stiffener is desirably positioned relative to the flaps and rings such that in use when the sleeve is tightened, the rings are located towards the one side of the stiffener (said side of the stiffener being distant to the flaps), in particular the elongate stiffener is positioned relative to the ring and flaps such that in use when the sleeve is tightened, the stiffener is essentially located between the rings and flaps. The stiffener is located between two layers, an inner layer (6) may of a resilient material (e.g. a spacer or foam material) and an upper layer (36) made of an appropriate covering material.

In the exemplary embodiment of FIG. 1, each ring (16) is connected to the closure element (5), in particular to the outer surface of the closure element, by a strap (17). From the cross-sectional view in FIG. 2, it can be seen that one end of the strap bears the ring and the other end is attached (either directly or indirectly; favorably fixedly), to the closure element, in particular to the outer surface thereof, such that the strap extends between the closure element and the ring in substantially the transverse direction relative to the sleeve. The end of strap which is attached to the closure element is desirably located proximal to the pairs of flaps, in particular proximal to the axis of hinged movement of the exterior flap, while the end of the strap which bears the ring is located distal to the pair of flaps.

Desirably straps comprise an expandable strap portion comprising a material having elasticity in at least the transverse direction (relative to the sleeve) and being configured and arranged such that when the expandable strap portion is in its non-expanded state (e.g. when the compression system is not in use) there is exteriorly a loop of material rising outwardly and when, in use when the closure element is attached to the sleeve and tension is provided in the transverse direction of the sleeve, the expandable strap portion expands in the transverse direction and the loop flattens (eventually disappearing).

Returning to the exemplary embodiment depicted in FIG. 1, in particular to the cross-sectional view of FIG. 2, it can be seen that each strap (17) include an expandable portion (21) that is configured with a loop (20) towards the exterior and rising outwardly. In particular, it can be seen that from the top, the indicating loop has the general form of a mound or a hump, while the loop-like form can be best seen in cross-sectional view shown in FIG. 2 which like FIG. 1 shows the expandable strap portion in its non-expanded state.

It can also be seen that the expandable portion of the strap favorably comprises two layers, an outer layer of material (18) and an inner layer of material (19) and wherein the inner layer of material is affixed to the outer layer of material, so as to provide a loop of outer-layer-material (i.e. loop (20)) above the inner layer when the expandable strap portion is in its non-expanded state, and which in use under the provision of tension and accordingly expansion of expandable strap portion in the transverse direction, respectively, can flatten.

For those embodiments where the expandable portion of the strap includes two layers, favorably the product of the modulus of elasticity (in the transverse direction) of the inner-layer-material times the thickness of the inner-layer material is equal to or less than the product of the modulus of elasticity (in the transverse direction) of the outer-layer-material times the thickness of the outer-layer material. More favorably, the product of the modulus of elasticity of the inner-layer-material times the thickness of the inner-layer-material is at least a factor of two times, more favorably at least a factor of four times, lower the product of the modulus of elasticity of the outer-layer-material times the thickness of the outer-layer-material, so that the transition from a pronounced loop to a completely flattened out loop does not require too much elongation in terms of length. Favorably at least one of the outer-layer- and inner-layer-materials has elasticity in at least the transverse direction, more favorably inner-layer-material has elasticity in at least the transverse direction.

Modulus of elasticity (also called elastic modulus) may be determined in accordance to ASTM D 882-09 entitled "Standard Test Method for Tensile Procedure of Thin Plastic Sheeting". It is to be noted that although the standard expressly states that it covers the determination of tensile properties of plastics in the form of thin sheeting, it has been found that the described test method and determination of modulus of elasticity may be suitably used in regard to materials suitable for use in compression devices described herein.

Desirably the product of the modulus of elasticity (in the transverse direction) of the material of the loop (e.g. the outer-layer-material in the two-layer expandable strap portion) times the thickness of the material of the loop is favorably at least 90% of the product of the modulus of elasticity (in the transverse direction) of the main material times the thickness of the main material, in particular the product of the modulus of elasticity of the material of the loop (e.g. the outer-layer-material in the two-layer expandable strap portion) times the thickness of the material of the loop is equal to or greater than the product of the modulus of elasticity of the main material times the thickness of the main material.

Returning to the exemplary embodiment of FIG. 1, each fastening band comprises a proximal end portion (22) and a distal end portion (24) being connected by an inner band portion (23). In the exemplary embodiment shown here in FIG. 1, the proximal end portions (22) are fixedly attached (e.g. via adhesive, bonding, or stitching) to the first lateral side region (13) of the sleeve. The fastening bands (2) are attached (here fixedly attached, and in alternative embodiments releasably attached) onto the sleeve such each band extends in substantially the transverse direction of the sleeve, with its distal end portion (24) positioned away from the central portion (14) of the sleeve. It can be seen in the exemplary embodiment that proximal end portions of the fastening bands may be bridged and/or integral to one another for ease in assembling the set of fastening bands onto the sleeve and/or for increasing the security of attachment of the fastening bands to the sleeve. It can be appreciated that each band in its extended configuration has a first major surface (34, not numbered on FIG. 1) facing inwardly and a second major surface (33) facing outwardly and since in this exemplary embodiment the proximal end portions of the bands are attached to the outer surface (3) of the first lateral side region (13), the first major surface across the width of the fastening band is located towards the outer surface of the sleeve and a second major surface is located away from the outer surface of the sleeve. The second major surface (33) at the distal end portion (24) of the band favorably comprises mechanical (e.g. male) fastening elements (25). In the illustrated exemplary embodiment, the second major surface at the proximal end portion (22) of the fastening bands has a structure or is provided with a structure (26) that is adapted to be engaged by said mechanical (e.g. male) fastening elements (e.g. a loop engagement material). The second major surface at the inner band portion of the fastening band may also have a structure or is provided with a structure (26) that is adapted to be engaged by said mechanical (e.g. male) fastening elements on the second major (outer) surface (33) at the distal end portion (24).

In alternative embodiments, the outer surface of at least the first lateral side portion of the sleeve may in addition or alternatively have a structure or be provided with a structure that is adapted to be engaged by the mechanical fastening elements on the second major surface of the distal end portion of the fastening bands. For those embodiments in which the outer surface of at least the first lateral side portion of the sleeve comprises an engaging structure rather than the proximal end portion of the fastening bands, the proximal end portion can be configured much smaller than that shown in exemplary embodiment of FIG. 1. This can be appreciated from the exemplary embodiment depicted in FIG. 5. In this embodiment like the embodiment of FIG. 1, the second major surface (33) at the distal end portion (24) of the fastening bands (2) favorably comprises mechanical fastening elements (25), in particular male fastening elements (e.g. hook-shaped or mushroom shaped fasteners), while now the outer surface (3) of the first lateral side region (13) is provided with a structure (29) that is adapted to be engaged by said mechanical (e.g. male) fastening elements (e.g. a loop engagement material). See also FIG. 6. It will be appreciated that in alternative embodiments, instead of having the two lateral side regions each being provided with (e.g. laminated to) e.g. a loop engagement material, the entire outer surface of the sleeve may be provided with such a material. Returning to the exemplary embodiment depicted in FIG. 5, it can be seen that the proximal end portions (22) of the fastening bands (2) do not include an engaging structure and are much smaller in size in the transverse direction, being configured to sufficiently allow for the attachment (typically fixed attachment) of the fastening bands to outermost portion of the first lateral side region (13) along and adjacent to the first lateral side edge (9). It will be appreciated that in such embodiments the proximal end portions of the fastening bands could alternatively be attached onto the inner surface of the sleeve, again along and adjacent to the first lateral side edge.

The exemplary embodiment depicted in FIG. 7 is an example of a compression system (100) where the fastening bands (2) are releasably attached to the outer surface (3) of the sleeve (1). This exemplary compression system is similar the exemplary embodiment depicted in FIG. 1, where the secondary closure element (5) is the same and the sleeve (1) and fastening bands differ to e.g. allow releasable attachment of the latter to the former. In particular in this exemplary embodiment, the first major (inner) surface (34) at the proximal end portion (22) of the fastening bands (2) is provided with mechanical fastening elements (in particular male fastening elements) (27) and the entire outer surface (3) of the sleeve (1) is provided e.g. via lamination of an appropriate material (e.g. a loop engagement material), with a structure (38) that is adapted to be engaged with said mechanical (male) fastening elements (27). This is best seen in FIG. 8, showing a cross-sectional view of the sleeve in FIG. 7, showing how the inner surface (34) at the proximal end portion (22) of the fastening band is releasably attached to the outer surface (3) at first lateral side region (15) of the sleeve (1). It will be appreciated that favorably the engaging structure (38) provided on the outer surface of the sleeve is adapted to be engaged with the mechanical (male) fastening elements (61) provided on the exterior flap (51) of the secondary closure element (5). In this exemplary embodiment, both the first and second lateral side regions (13, 15) of the sleeve are desirably configured such that they are trimmable, and as mentioned above such a configuration allows for an advantageously high degree of freedom in regard to width and/or circumference adjustment especially for those users having an unusual limb width or circumference where a custom sizing normally would be required.

Regardless of whether the fastening bands are fixedly attached or releasably attached to the first lateral side region of the sleeve, it may be advantageous (e.g. for ease in production or assembly purposes) in that the first lateral side region, the central region and second lateral side region are configured the same, i.e. the outer surface at each region has a structure or is provided with a structure that is adapted to be engaged by at least the mechanical fastening elements on the inner surface of the exterior flap, in particular by both the mechanical fastening elements on the inner surface of the exterior flap(s) and on the second major surface at the distal end portion of the fastening bands, and in the event of releasably attached fastening bands, then more particularly by all three types of the mechanical fastening elements, i.e. those on the inner surface of the exterior flap(s), those on the second major surface at the distal end portion of the fastening bands and those on the first major surface at the proximal end portion of the fastening bands. For embodiments with fixedly attached fastening bands, the mechanical fastening elements on the inner surface of the exterior flap(s) and on the second major surface at the distal end portion of the fastening bands may be identical. For embodiments with releasably attached fastening bands, as mentioned above mechanical fastening elements on the second major surface at the distal end portion of the fastening bands and on the first major surface at the proximal end portion of the fastening bands are favorably different, where the latter ones (i.e. second band fasteners) and the relevant engagement structure provided a stronger fastening (e.g. higher peel strength) that the former ones (i.e. the first band fasteners) with same engagement structure. For such embodiments the mechanical fastening elements on the inner surface of the exterior flap(s) may be identical to either the second band fasteners or the first band fasteners.

The exemplary embodiment depicted in FIGS. 9 and 10 is an example of a compression system (100) where the fastening bands (2) are fastened directly onto appropriate complementary engaging structure (55) provided on the secondary closure element (5). In addition, the fastening bands are integral with the first lateral side region (15) of the sleeve (1). In regard to the latter, it can be seen in FIG. 9 to the right that the fastening bands (2) extend in substantially the transverse direction of the sleeve out from the first lateral side edge (9) of the sleeve (1). As mentioned above, in such cases the first lateral side edge of the sleeve will be understood to run along a line (marked in FIG. 9 with a dashed line and labelled E) including the outer edges of the first lateral side region (15) of the sleeve located between fastening bands (9-1) and, if applicable, next to the uppermost and/or lowermost fastening bands and the boundary (9-2) between the first lateral side region of the sleeve and the fastening band. Referring to FIG. 10 to the right, it can be seen that the first major (inwardly facing) surface (44) at the distal end portion (24) of the fastening bands is provided with a mechanical (male) fastening elements (56). It will be appreciated that in comparison to the exemplary embodiments including rings, the extent of which the fastening bands extend over the first lateral side edge will normally be much less. Looking at the left side of FIGS. 9 and 10, it can be seen that in the exemplary embodiment the outer surface of the secondary closure element (5) is provided with a structure (55) that is adapted to be engaged by the mechanical fastening elements on the first major surface of the distal end portion of the fastening bands, e.g. a loop engagement material. In particular an individual patch of said engaging structure is provided for each of the fastening bands, wherein the pairs of flaps (50) extend lengthwise to one side of the series of engaging structure patches. Similarly to the other exemplary embodiments described above, the axis (A) for hinged movement of the exterior flaps (51) is positioned proximal to said engaging structure, and in use, when the closure element is attached to the sleeve along the second lateral side edge (10) of the sleeve, the engaging structure for the fastening bands is located distal to the second lateral side edge. It will be appreciated that in alternative embodiments, a single large section of engaging structure could be provided or the outer surface of the secondary closure element could have inherently have a structure that can engaged the fastening elements.

It will be appreciated that in each of the exemplary embodiments depicted in FIGS. 1, 5, 7 and 9, the flaps comprise web laminates, whereby the relevant portion of the inner surface of the outer web material forming the flap is provided with mechanical fastening elements via lamination of an appropriate web- or tape-like fastener material onto outer web material. In alternative embodiments, the pair of flaps may be favorably injection molded components.

To further facilitate the provision of a favorable anatomic fit over the portion of the body part (e.g. the lower leg including the calf) of a user that is covered by the sleeve of the system in use, favorably the plurality of rings or fastening bands including the interstices between rings or bands, respectively extends over a height corresponding to at least 70% of the height of the sleeve from the upper to lower edge. Generally it is desirable that the plurality of rings or bands including the interstices between rings or bands, respectively extends a height corresponding from 70% up to and including 100%, and possibly greater than 100% of the height of the sleeve from the upper to lower edge. The height of the interstices between rings or bands may range from 0.1 mm to 7 cm, inclusive, in particular from 0.3 mm to 3 cm, inclusive, and more particularly from 0.5 mm to 2 cm.

Although not specifically shown in the exemplary embodiments depicted herein, compression systems described herein may be configured to include other structural elements, for example a foot portion extending from the sleeve, in particular extending from an appropriate portion of the lower edge of the sleeve. Such a foot portion may be configured and arranged in the form of a stir-up or alternatively such as foot portion may be configured to provide a more extensive covering of the foot. Moreover the sleeve and such a foot portion may be configured and arranged so as to provide a boot-like compression device, either closed or opened toed and/or either closed or opened heeled. Such a foot part may be provided integrally with the sleeve or alternatively as a separate component that can be attached to the sleeve by an appropriate fastening means, such as buttons, mechanical fasteners and the like. Compression devices may also include bladders or gel inserts to facilitate modification of circumferential size. In this regard, sleeves, for example, could be provided with double walls or interior pockets for such inserts so that such insert(s) may be inserted and/or removed as needed or desired.

The following examples further illustrate the practice of the present invention. The examples are not intended to limit the invention, which is defined in the appended claims.

Test Methods—Material Properties

Test Methodology for Elongation, Recovered Elongation and Initial Slope of Tension-Elongation Curve:

Elongation, Recovered Elongation as well as Initial Slope of Tension-Elongation Curve were determined through measurements with a constant rate of extension tensile testing machine based on BS EN 14704-1:2005 "Determination of the elasticity of fabrics,—Part 1: Strip tests: Method A, Knitted Fabrics". The data acquisition frequency (6.1 b.) was typically 60 data sets per second. The mentioned test method was applied with following variations and/or conditions:

(i) The data acquisition frequency was at least 8 per second, i.e. typically 60 per second (see 6.1 b); (ii) strip test specimens were cut with their length parallel to direction to be measured, i.e. strips were cut so that the length of specimen is parallel either to the machine direction (MD) or cross-web direction (CW) of the material (which depending on the particular orientation that the material is used in the sleeve may correspond either to the transverse/circumferential or longitudinal direction of the sleeve) for determinations in said machine or cross-web direction, respectively;

(iii) specimen size was 150 mm in length and 50 mm wide (see 8.2.2.1.1);

(iv) gauge length was set at 100 mm (see 9.2.1.1);

(v) extension and retraction rate was set at 100 mm/min (section 9.2.1.2);

(vi) required cycling limits were set to said gauge length and a fixed load of 10 N per cm width (which corresponds to 50 N for given specimen width) (see subsection 9.2.1.3);

(vii) on the first cycle as well as on final (i.e. fifth) cycle, the testing machine was set to hold at 10 N per cm width for 1 minute (see NOTE 2 of 9.3);

(viii) the recovery period was 30 min (see NOTE 3 of 9.3);

(ix) test specimens were preconditioned for 24 hours at 50% RH and 20° C.; and (x) the number of test specimens was three and with the following results:

(a) percent elongation (S) is [(extension (mm) at maximum force after the final ($5^{th}$) cycle and after 1 minute holding time−initial length)/initial length]×100 (referred to in the following as final elongation at 10 N/cm);

(b) percent recovered elongation (D) is (100−un-recovered elongation in percentage) and percent un-recovered elongation (C) is [(Q−P)/P]×100 where Q is the distance between applied reference marks (mm) after specified hold and recovery periods following the $5^{th}$ cycle and P is the initial distance between reference marks (mm); and (c) The initial slope of the tension-elongation curve was determined by calculating the difference quotient of the two data sets having tension (T) values the closest to 0.1N/cm and 0.9N/cm in the rising part of the fifth cycle of the tension-elongation curve, i.e. slope=$(T_2-T_1)/(S_2-S_1)$.

Test Methodology for Water Vapor Transmission Rate (WVTR)

The water vapor transmission rate of fabrics was determined according to test method DIN EN ISO 15106-part 1:2005 "Determination of Water Vapour Transmission Rate—Part 1 Humidity Detection Sensor Method" with the following parameters, conditions and/or variations to given method:

(i) 38° C.; water vapor difference 90%; relative humidity upper chamber 10%, relative humidity lower chamber 100% (see Table 1; parameter set 2 in Section 8);

(ii) a reference specimen Core Tex, 5000 g/($m^2 \cdot 24$ h), lot 071808; 16.11.2009;

(iii) circular diffusion area having a diameter of 10 mm;

(iv) one test specimen was used for measuring the WVTR from inside to outside ("inside" is the side of the material, which is designated to be directed to the limb) and one for measuring the WVTR from outside to inside. For each of the specimens, the measurement was carried out three times. The reported values are the averages.

(v) the specimens were die-cut with a die having a cutting circle of 30 mm diameter; the aluminum barrier film was cut with a die having a cutting circle of 10 mm diameter; sample cards from MRS Seitter GmbH. Version: MRS 0225; lot no.: 100604 were used;

(vi) test specimens were preconditioned for 24 hours at 50% RH and 23° C. prior to testing; and (vii) Easyperm WVPT 650M from Gintronic AG, Rüti, Switzerland, CH-8630 was used as measurement equipment; and the water vapor transmission rate is reported in g/($m^2 \cdot 24$ h).

Test Methodology for Air Permeability

The air permeability was determined according to test method ISO 9237-1995 with the following parameters:

(a) TexTest Instruments Zürich, Air Permeability Tester 3; FX was used as measurement equipment;

(b) test pressure was 200 Pa;

(c) the test area was 20 $cm^2$;

(d) five specimens were measured per material;

(e) test specimens were preconditioned for 24 hours at 50% RH and 23° C. prior to testing;

(f) test conditions were 50% RH and 23° C.;

(g) the measured values were displayed and recorded in liters/$m^2$/s (same dimension as mm/s); the air permeability R reported in units of cm/s; and (h) average and standard deviation were determined based on five single samples (taken from different locations of the fabric specimens) and reported together with the determined coefficient of variation and 95% confidence range.

Materials (as Main Material)

M1:

Laminate of a spacer fabric and a hook-engageable fabric, laminated with a hot melt urethane adhesive with a coating weight of approximately 60 g/$m^2$ and applied to allow for porosity. Warp knitted spacer fabric (basis weight of about 285 g/$m^2$) with the product number T7808-0300-1500-9005 marketed by Müller Textil, 51674 Wiehl, Germany under the trade designation 3MESH was used as the spacer fabric. Perforated Nylon™ fabric having one surface of unbroken loop (UBL) material (basis weight of about 90 g/$m^2$) with the product number WW983, marketed by Gehring Textiles Inc., Garden City, N.Y. 11530, USA as used as the hook engageable fabric. The lamination was done such that the UBL-side of the perforated fabric and the surface having the wider mesh structure of the spacer fabric formed the outer surfaces of the laminate material; the laminate having a total basis weight of about 435 g/$m^2$ and a thickness of 3.8 mm.

M2:

Laminate of a spacer fabric and a hook engageable fabric, laminated with a hot melt urethane adhesive with a coating weight of approximately 60 g/$m^2$ and applied to allow for porosity. Warp knitted spacer fabric (100% polyester with a basis weight of 288 g/$m^2$) with the product number SHR700/3 D3, marketed by Gehring Textiles Inc was used as spacer fabric. The UBL fabric with the product number WW983 of Gehring Textiles Inc was used as the hook engageable fabric. The lamination was done such that the UBL-side of the perforated fabric and the surface having the wider mesh structure of the spacer fabric formed the outer surfaces of the laminate material; the laminate having a total basis weight of about 438 g/$m^2$ and a thickness of 2.6 mm.

M3:

Laminate of a spacer fabric and a hook engageable fabric, laminated with a hot melt urethane adhesive with a coating weight of approximately 60 g/$m^2$ and applied to allow for porosity. Warp knitted spacer fabric with the product number SHR700/3 D3 of Gehring Textiles Inc. was used as the spacer fabric. The UBL material (UBL on both sides; basis weight about 137 g/$m^2$) with the product number WW1306, marketed by Gehring Textiles Inc was used as the hook engageable fabric. The lamination was done such that the surface with the wider mesh structure of the spacer fabric was laminated towards the UBL material WW1306; the laminate having a total basis weight of about 485 g/m² and a thickness of 3.2 mm.

M4:

Polyurethane foam laminate with patterned hook engageable textile on both sides, designated as OP.TRAF.6 nero acc. FILTRO S45 3,5+OP.TRAF.6 nero, from Sitip S.p.A. Industrie Tessili, Via Vall'Alta, 13; I—24020—Cene (BG) having a basis weight of about 300 g/m² and a thickness of 4 mm.

M5:

Warp knitted spacer fabric designated as Rete Big Hole, Nero, from Akkotex; Via dell'Impresa, 20; 36040 Brendola (Vicenza), Italy, the fabric having an approximately 4 mm wide, open hexagon pattern on both surfaces and the fabric having a basis weight of about 261 g/m² and a thickness of 3.5 mm.

M6:

Warp knitted spacer fabric with the product number 6004 marketed by Müller Textil under the trade designation 3MESH having a basis weight of about 314 g/m² and a thickness of 3 mm.

R7:

Black two-layer laminate consisting of a spacer fabric and a hook-engageable layer surface from Ball & Son Limited (Trading as Baltex) (Registered No 535664), registered office Burr Lane, Ilkeston, Derbyshire DE7 5JD; basis weight of about 474 g/m² and a thickness of 3.8 mm

R8:

Laminate of a spacer fabric and a micro-hook engageable fabric, laminated with a hot melt urethane adhesive with a coating weight of approximately 60 g/m² and applied to allow for porosity. Warp knitted spacer fabric (basis weight about 285 g/m²) with the product number T5957-0300-1600-9005 marketed by Müller Textil under the trade designation 3MESH was used as spacer fabric, while the UBL-fabric with the product number WW983 of Gehring Textiles Inc was used as the micro-hook engageable fabric. The lamination was done such that in the resulting laminate, the UBL-side of the perforated fabric and the surface having the wider mesh structure of the spacer fabric formed the outer surfaces of the laminate material; the laminate having a total basis weight of about 470 g/m² and a thickness of 3.8 mm.

C1:

Fabric of the compression product marketed by Circaid Medical Products, Inc. San Diego, Calif. 92123, USA under the trade designation JUXTACURES having a basis weight of about 575 g/m² and a thickness of 2.5 mm.

Material Properties Testing Results

TABLE 1

Elongation and Recovered Elongation

| Material | Final Elongation (%) at 10 N/cm | | Sum of MD + CW | Recovered Elongation (%) | |
|---|---|---|---|---|---|
| | MD | CW | | MD | CW |
| M1 | 14 | 23 | 37 | 100 | 98 |
| M2 | 16 | 28 | 44 | 99 | 100 |
| M3 | 25 | 39 | 64 | 99 | 100 |
| M4 | 28 | 33 | 61 | 100 | 100 |
| M5 | 18 | 22 | 40 | 100 | 100 |
| M6 | 28 | 7 | 35 | 100 | 100 |
| R7 | 14 | 17 | 31 | 100 | 98 |
| R8 | 6 | 9 | 15 | 100 | 100 |
| C1 | 43 | 61 | 104 | 99 | 87 |

TABLE 2

Initial Slope of Tension-Elongation Curve for Materials having a Maximum Elongation in one Direction of 35% or less

| | Slope (N/(cm · %)) between 0.1 N/cm and 0.9 N/cm | |
|---|---|---|
| Material | MD | CW |
| M1 | 0.61 | 0.33 |
| M2 | 0.32 | 0.21 |
| M3 | 0.14 | 0.17 |
| M4 | 0.29 | 0.19 |
| M5 | 0.14 | 0.15 |
| M6 | 0.14 | 0.54 |
| R7 | 3.38 | 1.14 |
| R8 | 2.31 | 0.93 |

The tension versus elongation curves measured for each of the materials M1 to M6, R7 and R8 are illustrated in FIGS. 13 A to H, respectively.

In use in a sleeve as described herein, the machine direction of the M3 material would be advantageously oriented in the transverse direction of the sleeve. For M1, M2, M4 to M6 materials, either the machine direction or the cross-web direction could be favorably used along the transverse direction of the sleeve. For such situations, it has been found advantageous to use the material direction having the lower initial tension-elongation slope in the transverse direction of the sleeve.

TABLE 3

Determination of Water Vapor Transmission Rate

| | WVTR (g/(m² · 24 h)) | |
|---|---|---|
| Material | from inside out[1] | from outside in[2] |
| M1 | 3353 | 3197 |
| M2 | 3245 | 3311 |
| M3 | 3001 | 3036 |
| M4 | 3055 | 2962 |
| M5 | 4164 | 4121 |
| M6 | 3448 | 3488 |
| R7 | 2566 | 2702 |
| R8 | 3283 | 3291 |
| C1 | 2641 | 2564 |

[1]Here during WVTR-testing, the side of the material that would be on the interior of a compression system was placed towards the water vapor feed.
[2]Here during WVTR-testing, the side of the material that would be on the exterior of a compression system was placed towards the water vapor feed-

TABLE 4

Determination of Air Permeability

| Material | Average (cm/s) | Coefficient of variation (%) | 95% confidence interval (cm/s) | |
|---|---|---|---|---|
| | | | Lower limit | Upper limit |
| M1 | 244(12) | 4.9 | 220 | 267 |
| M2 | 198(10) | 5.0 | 179 | 218 |
| M3 | 124(5.7) | 4.6 | 112 | 135 |
| M4 | 258(3.2) | 1.2 | 252 | 264 |
| M5 | 791(7.3) | 0.9 | 776 | 805 |
| M6 | 495(28) | 5.8 | 439 | 551 |
| R7 | 208(13.2) | 6.3 | 182 | 234 |
| R8 | 234(7.4) | 3.2 | 219 | 248 |
| C1 | 21(2.1) | 10.2 | 16 | 25 |

Test Methods Towards Compression Relevant Properties

The following test methods were created and used to assess the materials for compression system relevant properties. It is known that the efficacy of compression therapy depends mainly on the exerted pressure and on the stiffness of the material used in the compression system. The first method listed below provides a simple in-vitro method of assessing exerted pressure and stiffness of a material by mimicking the well known one-cm-increase in the leg circumference upon standing up from a lying position and measuring the pressure difference there between. The second method provides a simple in-vitro method of assessing shape-conformability of a material, a property of which is, in turn, related an ability of a material to exert pressure, in particular over an irregular surface, uniformly.

Test Methodology for In-Vitro Static Stiffness Index

A cylinder of 4 cm radius and 23 cm length made of polyacetal and cut into two halves along the rotation axis was used to simulate a limb. The cylinder halves were assembled with two screws and corresponding nuts located in two holes running perpendicularly to the rotation axis of the cylinder at a distance of 3.5 cm away from the ends of the cylinder. Two additional screws and corresponding nuts were provided in two holes running in parallel to the other screws at a distance of 5 cm away from the ends of the cylinder. The outer screws were used as counter screws to the inner screws to pre-adjust a gap between the two cylinder halves of 5 mm. With the inner screws, the cylinder halves could be separated to the pre-adjusted distance (5 mm) by turning to the limit given by the outer counter screws. Two elastic rings put around the cylinder at a distance of 1 cm away of the edges kept the cylinder halves touching each other, when the inner screws were moved out. This mechanism allowed for easy and reproducible alteration of the cylinder circumference with a difference of one centimeter. A Pico Press pressure sensor from MicroLab Elettronica, Italy, of approx. 50 mm diameter was fixed centrally on the outside of one cylinder half with a stripe of tape (3M #471 PVC tape) centrally between the screws. The tape did not touch the bladder of the sensor itself but the end of the connected tube. The sensor was connected with a Pico Press pressure measurement unit from MicroLab Elettronica Sas, Roncaglia di Ponte San Nicolò (PD), Italy.

Strip test specimens 25 cm in length and 15 cm in width were cut with their length parallel to direction to be measured, i.e. strips were cut so that the length of specimen is parallel to the material manufacturing direction to be measured, i.e. the machine direction (MD) or cross-web direction (CW) of the material. The following procedure was carried out at 23° C., 50% RH after having stored the specimens for at least 24 hours at same conditions.

Prior to wrapping a test specimen around the cylinder, the gap between the cylinder halves was set to zero and the sensor was calibrated. The test specimen was wrapped around the cylinder, such that, if applicable the hook engageable surface faced outwardly and the two narrow ends of the textile specimen were positioned towards one another and on the side of cylinder opposite to the sensor. The two ends of the test specimen were pulled uniformly towards one another and then fixed, so that an initial pressure reading between 11 mmHg and 15 mmHg was provided on the sensor. For those test specimen having a hook-engageable outer surface, the ends were then held together by means of a 5 cm×15 cm large piece of Velcro hook band #88 from Velcro USA, Inc., 406 Brown Avenue, Manchester, N.H. 03103, USA, where the longer side of the Velcro hook band #88 was positioned in parallel to the ends of the test specimen. For the other test specimens, the ends of the test specimen were sewn together and, after sewing if necessary, to achieve the desired initial pressure reading, one or more bars made of solid, non-compressible material having different diameters were inserted between test specimen and cylinder until the desired pressure reading was reached. The bars remained in place during the measurements.

Then, the screws were turned until a gap of 5 mm between the cylinder halves was obtained. For turning of the screws (and just for this), the edge of the overlaying textile specimen—which covered the screws—had to be locally moved by up to 2 cm on each edge side so that the wrench could reach the screws. After screw turning, the edges were moved back to the original location. After this step, the cylinder halves were brought together again and it was checked, whether the resulting pressure reading was in the range of 10 mmHg and 15 mmHg. If this was not the case, the last two steps were repeated. If it was the case, the cylinder halves were separated to 5 mm distance again and after holding a minute the pressure was read and recorded as the "expanded pressure". Then, the gap between the cylinder halves was closed again and after holding a minute, the pressure was read and recorded as the "resting pressure".

The in-vitro static stiffness index was calculated by subtracting the resting pressure reading from the expanded pressure reading and dividing the resulting value by the overall circumference increase in centimeters, i.e. 1 cm.

Test Methodology for Shape Conformability

Figure 12:
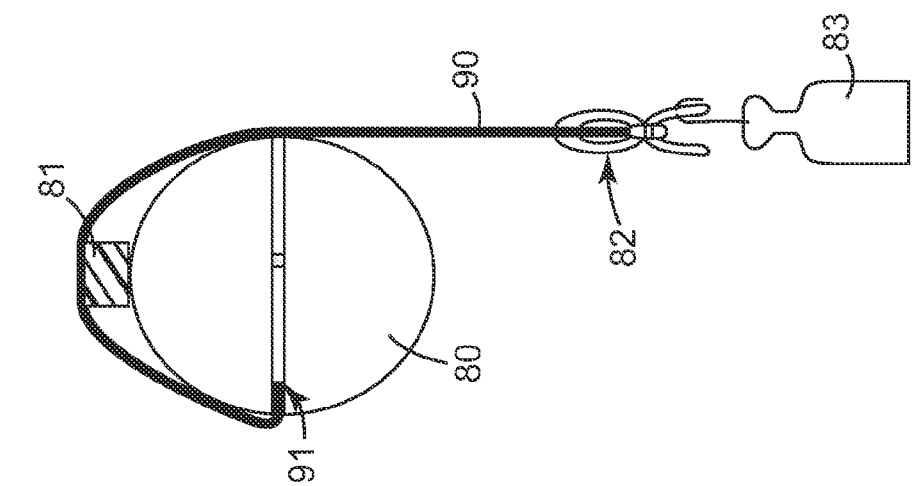
FIG. 12 shows a cross-sectional view exemplary test configuration depicted in FIG. 11.
Figure 11:
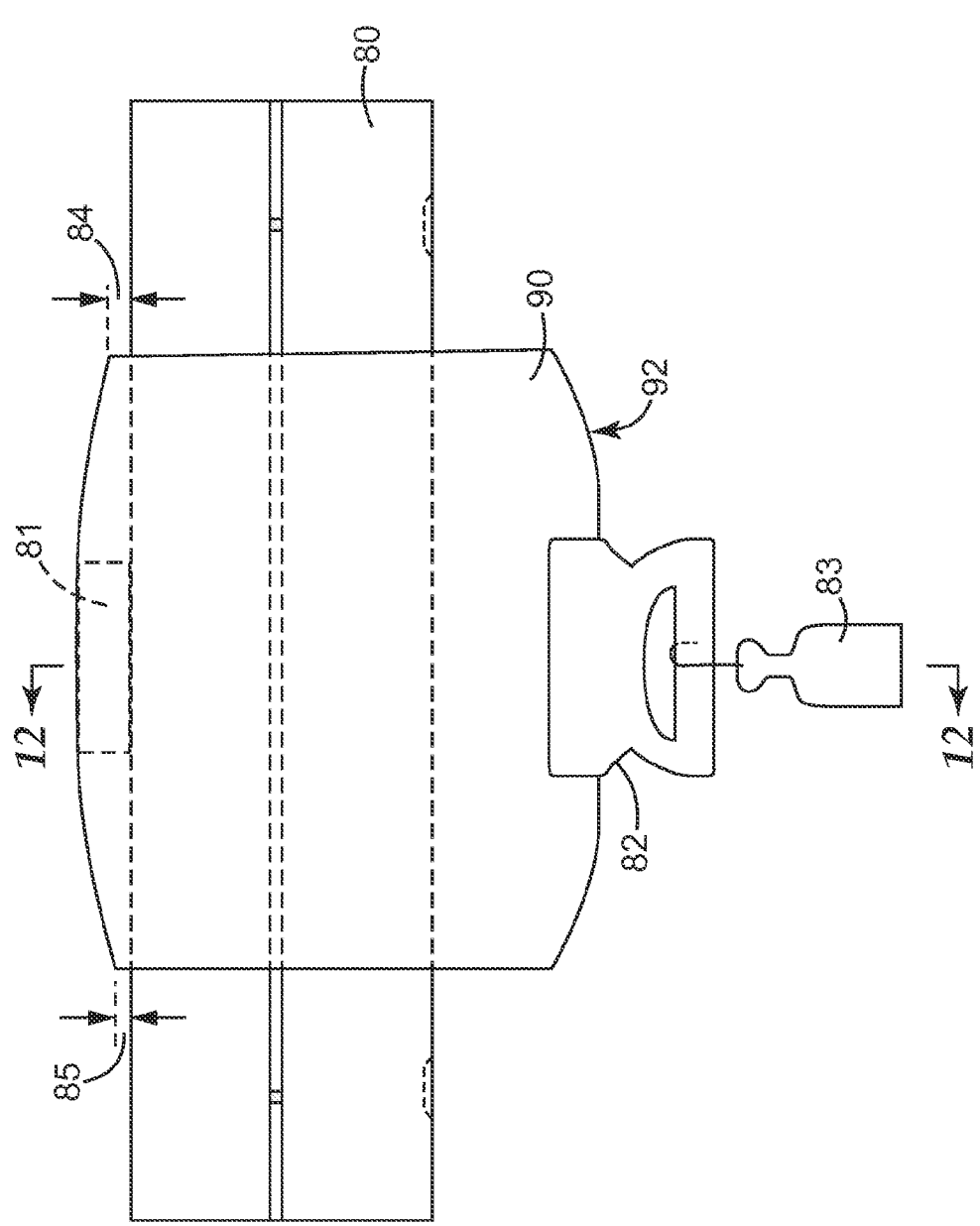
Figure 13A:
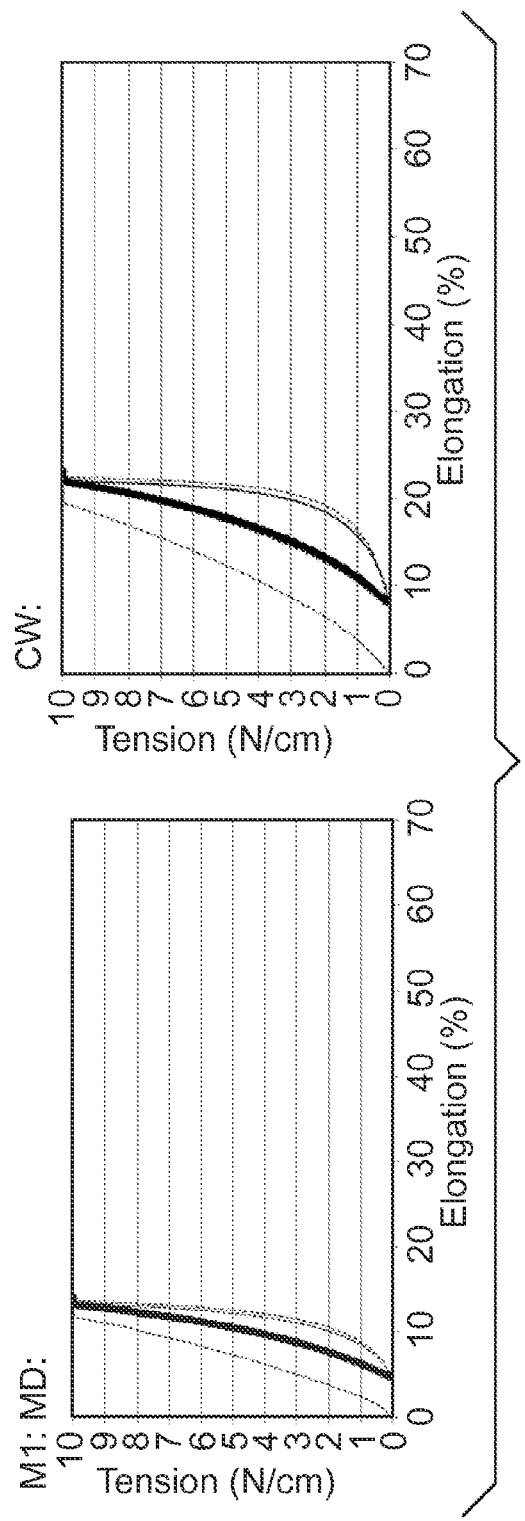
FIGS. 13 A to H represent the measured tension versus elongation curves for a series of material samples relative to their machine direction (MD) and cross web direction (CW).
Figure 13B:
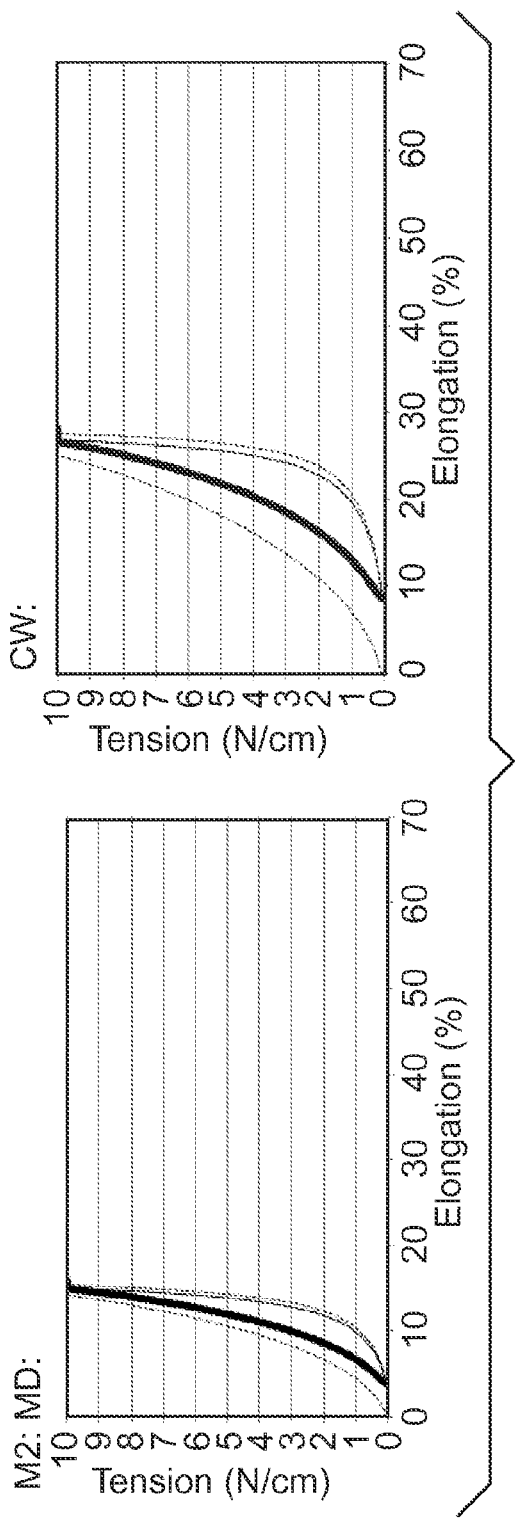
Figure 13C:
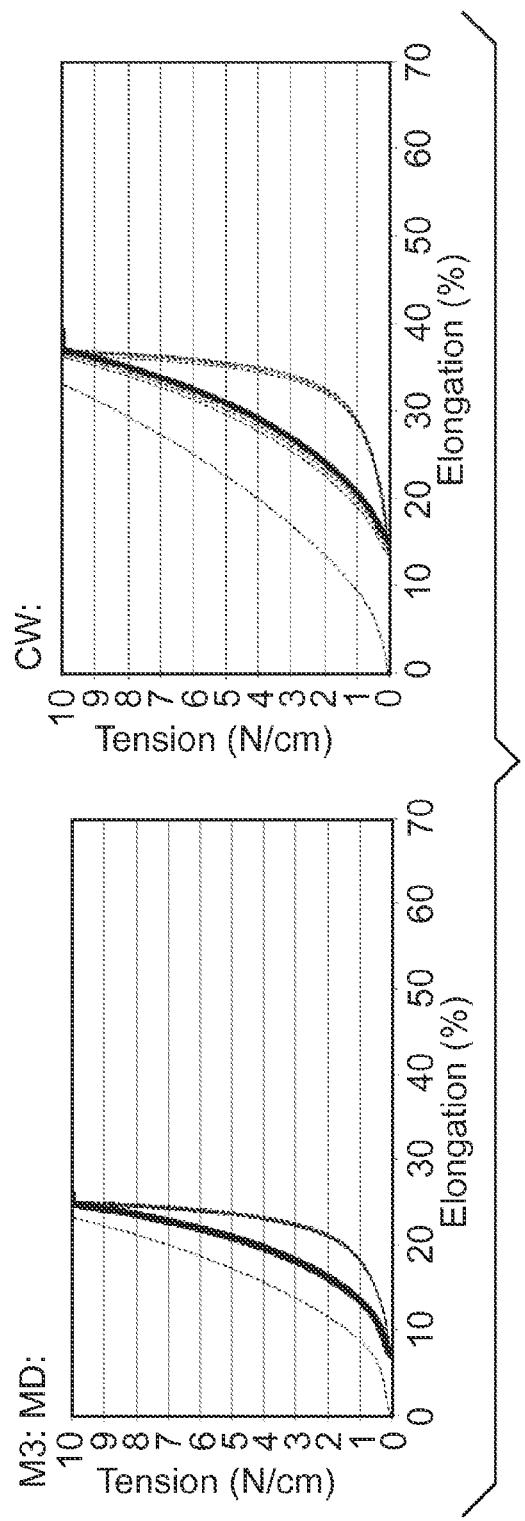
Figure 13D:
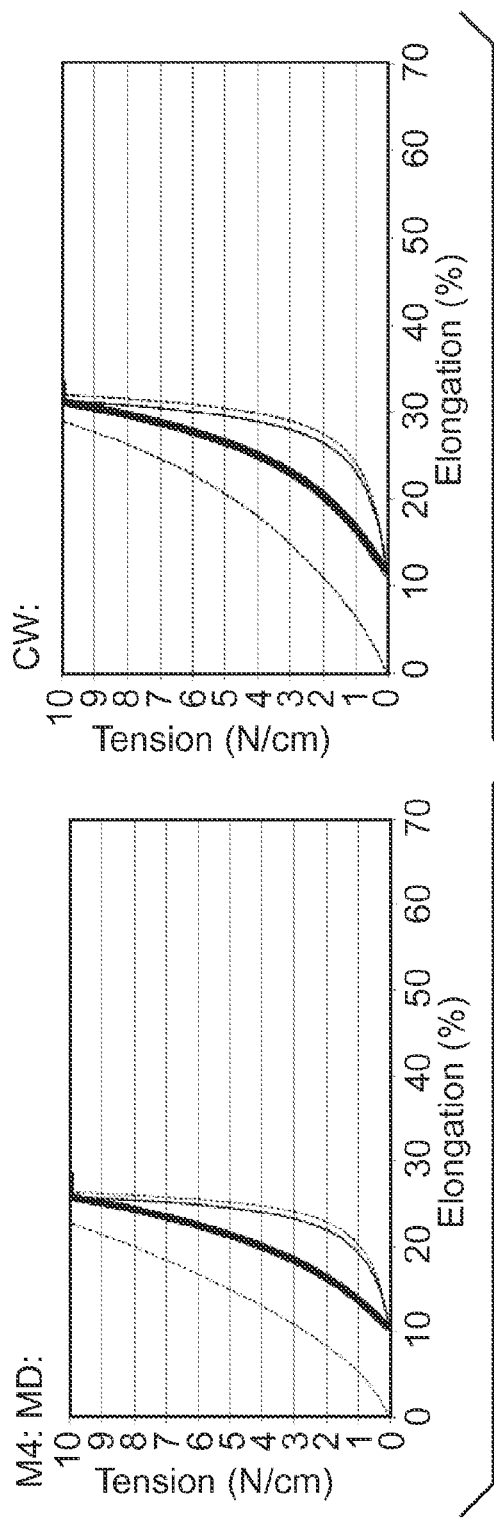
Figure 13E:
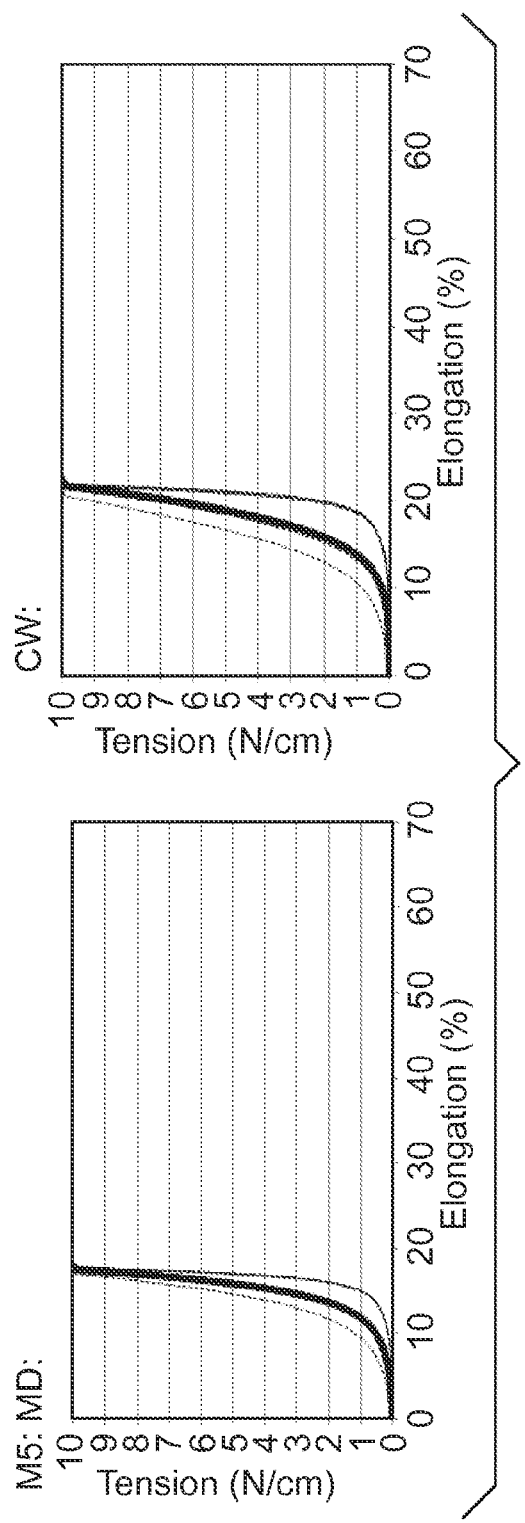
Figure 13F:
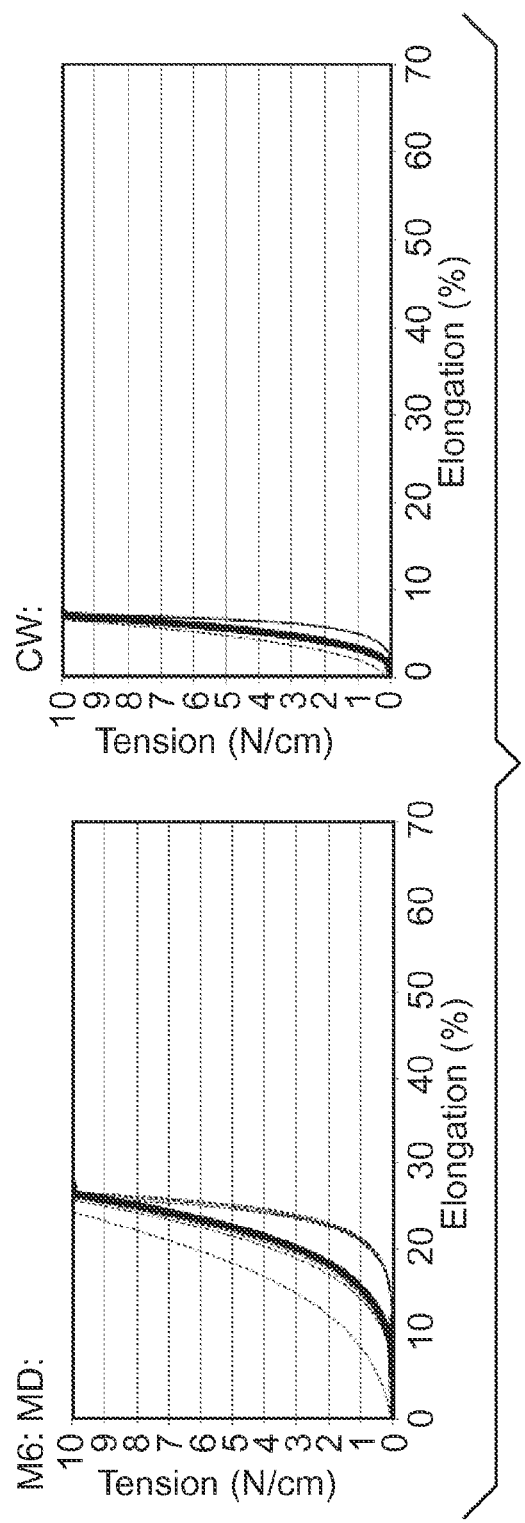
Figure 13G:
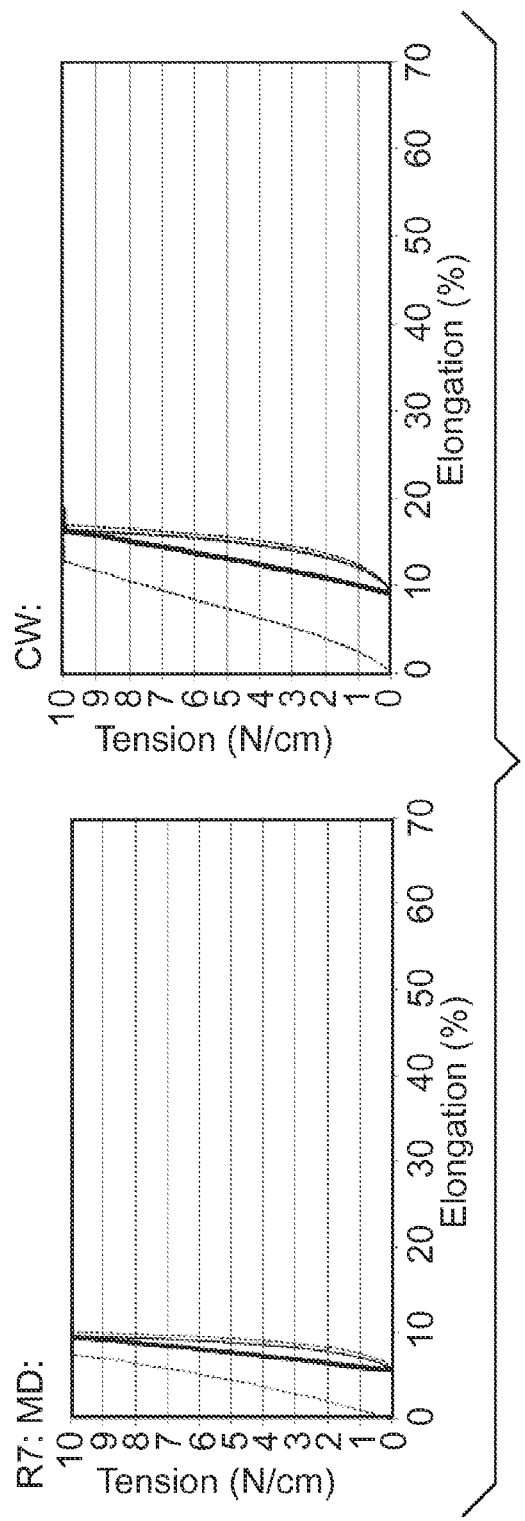
Figure 13H:
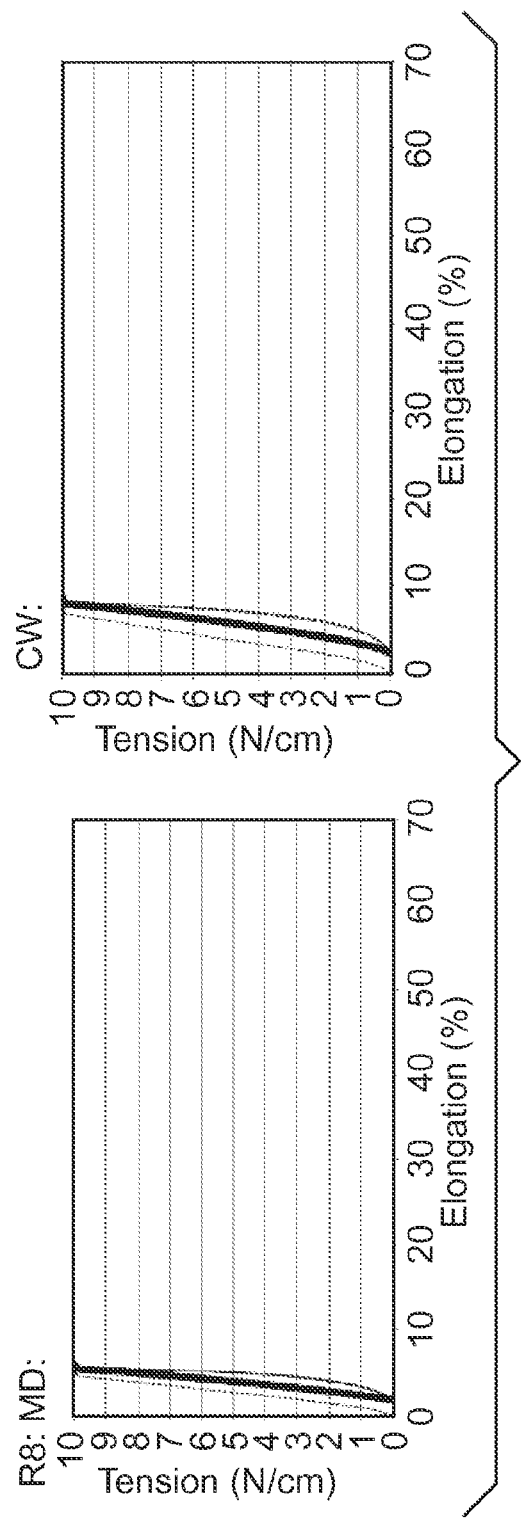

The two-part adjustable cylinder described in the in-vitro SSI test was used; the cylinder (80) in conjunction with the set up to measure shape conformability being schematically illustrated in FIGS. 11 and 12. To simulate strong surface contours, such as those found on the surface of a limb, a box-shaped eraser (81; referred to as "cuboid" in the following), supplied by Lyreco (EAN code 3662168013161) trimmed to the size of the size 50 mm×23 mm×13 mm was attached by means of 3M vinyl tape #471 to the outside of one cylinder half such that the long side was in parallel to the rotation axis of the cylinder and the height was 13 mm. The cuboid was centrally positioned on the cylinder half with respect to the long and the circumferential directions of the cylinder half.

Strip test specimens 25 cm in length and 15 cm in width were cut with their length parallel to direction to be measured, i.e. strips were cut so that the length of specimen is parallel to the material manufacturing direction to be measured, i.e. the machine direction (MD) or cross-web direction (CW) of the material. The following procedure was carried out at 23° C., 50% RH after having stored the specimens for at least 24 hours at same conditions.

Prior to the positioning a test specimen (90) on the cylinder (80), the cylinder was rotated so that the cuboid faced straight down towards the tabletop and the interface between the two cylinder halves parallel the tabletop. One narrow end (91; only visible in FIG. 12) of the test specimen was positioned centrally and clamped over the length of one centimeter between the two cylinder halves, such that the specimen hung downwardly not contacting the cylinder surface. (For specimens having a hook-engageable surface, said surface was positioned away from the cylinder surface.) At the other narrow end (92) of the test specimen, a 6 cm-wide metal clamp (82) (weight 0.048 kg) was attached and onto this clamp a 1.5 kg weight (83) was then attached.

As soon as the weight (83) was attached, the cylinder (80) was rotated manually by 180° within one to two seconds, so that the test specimen (90) covered the cylinder half provided with the cuboid (81), so that the test specimen draped over the contour surface and down towards the tabletop. This configuration is shown in FIGS. 11 and 12. Then following a holding period of about 1 minute the height of any gaps (84, 85) were measured. In particular at a position parallel to the long face of the cuboid, said face running along the length of the cylinder and being near to the weighted end of the test specimen, the distance between the outer surface of the cylinder and the interior surface of the test specimen at the two specimen edges was measured by means of a caliper. The reported value is the average between two measured values.

Compression Relevant Properties Testing Results

TABLE 5

Determination of In-vitro Static Stiffness Index

| | MD | | | CW | | |
|---|---|---|---|---|---|---|
| Material | Resting (mmHg) | Expanded (mmHg) | In-vitro SSI (mmHg/cm) | Resting (mmHg) | Expanded (mmHg) | In-vitro SSI (mmHg/cm) |
| M1 | 12 | 72 | 60 | 13 | 46 | 33 |
| M2 | 14 | 65 | 51 | 13 | 47 | 34 |
| M3 | 13 | 58 | 45 | 13 | 44 | 31 |
| M4 | 13 | 35 | 22 | 13 | 35 | 22 |
| M5 | 11 | 51 | 40 | 12 | 44 | 32 |
| M6 | 10 | 50 | 40 | 11 | 110 | 99 |
| R7 | 12 | 45 | 33 | 14 | 55 | 41 |
| R8 | 12 | 80 | 68 | 13 | 79 | 66 |
| C1* | 13 | 22 | 9 | n.a. | n.a. | n.a. |

*test specimen taken from commercial product and measured relevant to transverse direction of the product

TABLE 6

Assessment of Shape conformability

Gap distances in mm

| Material | MD | CW | Average of MD and CW |
|---|---|---|---|
| M1 | 6 | 3.5 | 4.75 |
| M2 | 4 | 3.5 | 3.75 |
| M3 | 2 | 0.5 | 1.25 |
| M4 | 0.5 | 0.5 | 0.5 |
| M5 | 0.5 | 0 | 0.25 |
| M6* | 2 | 7 | 4.5 |
| R7 | 5.5 | 7 | 6.25 |
| R8 | 8 | 8.5 | 8.25 |
| C1* | 0 | 0 | 0 |

*surface with the more open pattern positioned outwardly

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A compression system for applying compression to a body part of a user comprising a sleeve for substantially covering a portion of the body part of the user, wherein the sleeve has a first lateral side edge and a second lateral side edge, wherein in the transverse direction from the first lateral side edge to the second lateral side edge the sleeve comprises a first lateral side region, a central region and a second lateral side region, wherein at least the central region of the sleeve comprises a material having elasticity in the transverse direction and longitudinal direction of the sleeve, said material having a maximum elongation in said transverse direction of the sleeve from 20% up to and including 35% under a load of 10 N per cm width and having tension and elongation characteristics in a first direction of the sleeve such that the slope of a tension-elongation curve in that region of the curve where the force per cm width ranges from 0.1 N/cm to 0.9 N/cm is equal to or less than 0.9 N/(cm·%), and wherein the compression system further comprises a releasable closure system, said closure system being configured and arranged relative to the sleeve, such that, in use, upon closure of the closure system the sleeve is restrained and tightened about the body part of the user.

2. The compression system according to claim 1, wherein said material has tension and elongation characteristics in a second sleeve direction such that the slope of a tension-elongation curve in that region of the curve where the force per cm width ranges from 0.1 N/cm to 0.9 N/cm is equal to or less than 0.50 N/(cm·%).

3. The compression system according to claim 1, wherein said material has tension and elongation characteristics in a second sleeve direction such that the slope of the tension-elongation curve is between 0.05 N/(cm·%) and 0.5 N/(cm·%).

4. The compression system according to claim 1, wherein said material has tension and elongation characteristics in the first direction of the sleeve such that the slope of the tension-elongation curve is equal to or less than 0.75 N/(cm·%).

5. The compression system according to claim 1, wherein said material has tension and elongation characteristics in the first direction of the sleeve such that the slope of the tension-elongation curve is between 0.05 N/(cm·%) and 0.9 N/(cm·%).

6. The compression system according to claim 1, wherein said first direction of the sleeve is the transverse direction of the sleeve.

7. The compression system according to claim 1, wherein the material has a maximum elongation in the longitudinal direction under a load of 10 N per cm width from 5% up to and including 70%.

8. The compression system according to claim 1, wherein a sum of maximum elongations of the material in the transverse and longitudinal directions of the sleeve under a load of 10 N per cm width is in a range from 10% up to and including 75%.

9. The compression system according to claim 1, wherein the material has a recovered elongation in the transverse direction and/or in the longitudinal direction of the sleeve equal to or greater than 90%.

10. The compression system according to claim 1, wherein the material has a bending length in the transverse and/or the longitudinal direction equal to or less than 20 cm; and/or wherein the material has a flexural rigidity in the transverse and/or the longitudinal direction equal to or less than 150 mN·cm.

11. The compression system according to claim 1, wherein the material has from an inner surface to an outer surface and/or from the outer surface to the inner surface an air permeability of 20 cm/sec according to test ISO 9237-1995 using at a test pressure of 200Pa.

12. The compression system according to claim 1, wherein the material has from its an inner surface to an outer surface a water vapor transmission rate equal to 1000 $g/(m^2 \cdot h)$ as measured according to ISO 15106, part 1.

13. The compression system according to claim 1, wherein the material has a basis weight equal to 100 $g/m^2$.

14. The compression system according to claim 1, wherein the sleeve and the closure system are configured and arranged such that in use, upon closure of the closure system, the first lateral side edge and second lateral side edge of the sleeve are drawn towards one another, but do not overlap.

15. The compression system according to claim 1, further comprising a first lateral side region of the sleeve is provided with a plurality of fastening bands in series along substantially the longitudinal direction of the sleeve, and wherein the fastening bands are integral with the first lateral side region of the sleeve such that the fastening bands extend in substantially the transverse direction of the sleeve out from the first lateral side region of the sleeve; or wherein each of the fastening bands comprise a proximal end portion, said proximal end portion being releasably or fixedly attached to the first lateral side region of the sleeve such that the fastening bands extend in substantially the transverse direction of the sleeve over the first lateral side region.

* * * * *

UNITED STATES PATENT AND TRADEMARK OFFICE
CERTIFICATE OF CORRECTION

PATENT NO. : 11,278,453 B2
APPLICATION NO. : 15/512133
DATED : March 22, 2022
INVENTOR(S) : Guido Hitschmann Page 1 of 1

It is certified that error appears in the above-identified patent and that said Letters Patent is hereby corrected as shown below:

In the Claims

Column 33
Line 3, In Claim 11, delete "at" between "using" and "a test".
Line 7, In Claim 12, delete "1000 g/(m$^2$.h)" and insert -- 1000 g/(m$^2$.24h) --, therefor.
Line 17, In Claim 15, delete "is" between "sleeve" and "provided".

Signed and Sealed this
Twenty-fifth Day of October, 2022

Katherine Kelly Vidal
*Director of the United States Patent and Trademark Office*